(12) United States Patent
Matula et al.

(10) Patent No.: US 7,804,595 B2
(45) Date of Patent: Sep. 28, 2010

(54) USING OPTICAL SCATTERING TO MEASURE PROPERTIES OF ULTRASOUND CONTRAST AGENT SHELLS

(75) Inventors: Thomas Matula, Kirkland, WA (US); Jingfeng Guan, Seattle, WA (US)

(73) Assignee: University of Washington, Seattle, WA (US)

( * ) Notice: Subject to any disclaimer, the term of this patent is extended or adjusted under 35 U.S.C. 154(b) by 1044 days.

(21) Appl. No.: 11/531,998

(22) Filed: Sep. 14, 2006

(65) Prior Publication Data

US 2007/0098232 A1    May 3, 2007

Related U.S. Application Data

(60) Provisional application No. 60/716,861, filed on Sep. 14, 2005.

(51) Int. Cl.
*G01N 21/49* (2006.01)
*A61B 8/08* (2006.01)
(52) U.S. Cl. .................. 356/338; 356/442; 424/9.52
(58) Field of Classification Search .................. None
See application file for complete search history.

(56) References Cited

U.S. PATENT DOCUMENTS 6,423,007 B2 * 7/2002 Lizzi et al. ............ 600/458

7,374,744 B2 * 5/2008 Schutt ............... 424/9.5

OTHER PUBLICATIONS

Wen-Shiang Chen, Thomas J. Matula, Lawrence A. Crum, The disappearance of ultrasound contrast bubbles: observations of bubble dissolution and cavitation nucleation, Ultrasound in Medicine & Biology, vol. 28, Issue 6, Jun. 2002, pp. 793-803, ISSN 0301-5629, DOI: 10.1016/S0301-5629(02)00517-3. (http://www.sciencedirect.com/science/article/B6TD2-4.*
Barber, Bradley P., and Seth J. Putterman. "Light Scattering Measurements of the Repetitive Supersonic Implosion of a Sonoluminescing Bubble" Physical Review Letters, vol. 69, No. 26. Dec. 28, 1992. pp. 3839-3842.
Church, Charles C. "The effects of an elastic solid surface layer on the radial pulsations of gas bubbles" J. Acoust. Soc. Am. 97 (3), Mar. 1995. pp. 1510-1521.

(Continued)

*Primary Examiner*—Gregory J Toatley, Jr.
*Assistant Examiner*—Rebecca C Slomski
(74) *Attorney, Agent, or Firm*—Ronald M. Anderson

(57) ABSTRACT

A system and method for determining bubble shell properties using optical scattering. One or more ultrasound contrast agent (UCA) bubbles is placed in an imaging volume and illuminated with a laser. The UCA is exposed to pressure variations (e.g., using pulses of imaging or therapeutic ultrasound), while optical scattering data are collected and processed. The scattering intensity is related to the radius of the UCA. Thus, changes in the radius due to varying pressure conditions results in variations in the scattering intensity. The collected data are processed to provide a radius versus time (RT) relationship. The RT relationship is fit to one or more conventional dynamic models. The fitted empirical data can be used to determine one or more UCA parameters, such as shear modulus and shell viscosity.

26 Claims, 18 Drawing Sheets

OTHER PUBLICATIONS de Jong, N., and L. Hoff. "Ultrasound scattering properties of Albunex microspheres" Ultrasonics vol. 31, No. 3. 1993. pp. 175-181.

Hansen, Gary M. "Mie scattering as a technique for the sizing of air bubbles" Applied Optics vol. 24, No. 19. Oct. 1, 1985. pp. 3214-3220.

Hoff, Lars, Per C. Sontum, and Jens M. Hovern. "Oscillations of polymeric microbubbles: Effect of the encapsulating shell" J. Acoust. Soc. Am. 107 (4), Apr. 2000. pp. 2272-2280.

Holt, Glynn R., and Lawrence A. Crum. "Mie scattering used to determine spherical bubble oscillations" Applied Optics vol. 29, No. 28. Oct. 1, 1990. pp. 4182-4191.

Khismatullin, Damir B., and Ali Nadim. "Radial oscillations of encapsulated microbubbles in viscoelastic liquids" Physics of Fluids vol. 14, No. 10. Oct. 2002. pp. 3534-3557.

Langley, Dean S., and Philip L. Marston. "Critical-angle scattering of laser light from bubbles in water: measurements, models, and application to sizing of bubbles" Applied Optics vol. 23, No. 7. Apr. 1, 1984. pp. 1044-1054.

Marsh, Jon N., Michael S. Hughes, Gary H. Brandenburger, and James G. Miller. "Broadband Measurement of the Scattering-to-Attenuation Ratio for Albunex at 37° C." Ultrasound in Med. & Biol. vol. 25, No. 8. 1999. pp. 1321-1324.

Marston, Philip L., Stuart C. Billette, and Cleon E. Dean. "Scattering of light by a coated bubble in water near the critical and Brewster scattering angles" SPIE vol. 925 Ocean Optics IX. 1988. pp. 308-316.

Moran, Carmel M., T. Anderson, S.D. Pye, V. Sboros, and W.N. McDicken. "Quantification of Microbubble Destruction of Three Fluorocarbon-Filled Ultrasonic Contrast Agents" Ultrasound in Med. & Biol. vol. 26, No. 4. 2000. pp. 629-639.

Morgan, Karen E., John S. Allen, Paul A. Dayton, James E. Chomas, Alexander L. Klibanov, and Katherine W. Ferrara. "Experimental and Theoretical Evaluation of Microbubble Behavior: Effect of Transmitted Phase and Bubble Size" IEEE Transactions on Ultrasonics, Ferroelectrics, and Frequency Control. vol. 47, No. 6. Nov. 2000. pp. 1494-1509.

Sboros, V., K.V. Ramnarine, C.M. Moran, S.D. Pye, and W.N. McDicken. "Understanding the limitations of ultrasonic backscatter measurements from microbubble populations" Phys. Med. Biol. 47. 2002. pp. 4287-4299.

Shi, William T., and Flemming Forsberg. "Ultrasonic Characterization of the Nonlinear Properties of Contrast Microbubbles" Ultrasound in Med. & Biol. vol. 26, No. 1. 2000. pp. 93-104.

Wolfrum, B., R. Mettin, T. Kurz, and W. Lauterborn. "Observations of pressure-wave-excited contrast agent bubbles in the vicinity of cells" Applied Physics Letters vol. 81, No. 26. Dec. 23, 2002. pp. 5060-5062.

Zhang, Dong, Xiu-Fen Gong, Jie-Hui Liu, Li-Zheng Shao, Xiao-Rong Li, and Qing-Lang Zhang. "The Experimental Investigation of Ultrasonic Properties for a Sonicated Contrast Agent and its Application in Biomedicine" Ultrasound in Med. & Biol. vol. 26, No. 2. 2000. pp. 347-351.

Allen et al., "Dynamics of therapeutic ultrasound contrast agents." *Ultrasound in Medicine and Biology* vol. 28, No. 6: 805-816, 2002.

Dayton et al., "Optical and acoustical observation of the effects of ultrasound on contrast agents." *IEEE Transactions on Ultrasonics, Ferroelectrics, and Frequency Control* vol. 46, No. 1: 220-232, 1999.

de Jong et al., "Higher harmonics of vibrating gas-filled microspheres. Part one: Simulation." *Ultrasonics* vol. 32, No. 6: 447-452, 1994.

de Jong et al., "Higher harmonics of vibrating gas-filled microspheres. Part two: Measurements." *Ultrasonics* vol. 32, No.6: 455-458, 1994.

Forsberg et al., "Effect of filling gasses on the backscattering from contrast microbubbles: Theory and in vivo measurements." *Ultrasound in Medicine and Biology* vol. 25, No. 8: 1203-1211. 1999.

Guan et al., "Using light-scattering to measure the response of individual ultrasound contrast microbubbles subjected to pulsed ultrasound in vitro." *Journal of the Acoustical Society of America* vol. 116, No. 5: 2832-2842, 2004.

Postema et al., "Ultrasound-induced encapsulated microbubble phenomena." *Ultrasound in Medicine and Biology* vol. 30, No. 6: 827-840, 2004.

Van der Meer et al., "Microbubble spectroscopy of ultrasound contrast agents." *Journal of the Acoustical Society of America* vol. 121, No. 1: 648-656, 2007.

* cited by examiner

TABLE I. Response curve parameters. $P^-_{peak}$ is the measured peak negative pressure, $\epsilon\mu_{sh}$ is the assumed shell parameter, $R_0$ is the fitted ambient radius, and $R_{max}$ is the resultant maximum radius.

| Figure | Agent | $\epsilon\mu_{sh}$ (nm Pa s) | Media | Source | $P^-_{peak}$ (kPa) | $R_0$ (μm) | $R_{max}$ (μm) | $R_{max}/R_0$ |
|---|---|---|---|---|---|---|---|---|
| Fig. 5(a) | Optison® | 6 | Water | UM4+[a] | 210 | 1.47 | 1.71 | 1.2 |
| Fig. 5(b) | Optison® | 6 | Gel | UM4+[a] | 340 | 1.50 | 1.93 | 1.3 |
| Fig. 6(a) | Optison® | 6 | Water | SET[b] | 70 | 1.27 | 1.4 | 1.1 |
| Fig. 6(b) | Optison® | 6 | Gel | SET[b] | 100 | 1.48 | 1.8 | 1.2 |
| Fig. 7(a) | Sonazoid® | 2 | Water | SET[b] | 130 | 1.4 | 2.1 | 1.5 |
| Fig. 7(b) | Sonazoid® | 2 | Gel | SET[b] | 190 | 1.1 | 2.0 | 1.8 |

[a]Ultramark 4Plus
[b]Single element transducer.

*FIG. 8*

TABLE II. Response curve parameters for evolving Sonazoid® microbubble in water. $\epsilon\mu_{sh}$ is the assumed shell parameter, $P^-_{peak}$ is the measured peak negative pressure, $R_0$ is the fitted ambient radius, and $R_{max}$ is the resultant maximum radius.

| Figure | $\epsilon\mu_{sh}$ (nm Pa s) | $P^-_{peak}$ (kPa) | $R_0$ (μm) | $R_{max}$ (μm) | $R_{max}/R_0$ |
|---|---|---|---|---|---|
| Fig. 9A | 2 | 130 | 1.20 | 1.58 | 1.32 |
| Fig. 9B | 2 | 130 | 1.50 | 1.96 | 1.31 |
| Fig. 9C | 2 | 130 | 1.90 | 2.39 | 1.26 |

*FIG. 10*

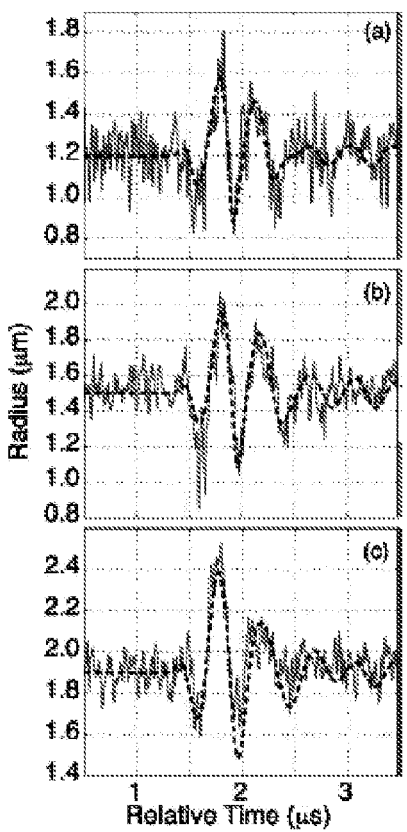
FIG. 9A
FIG. 9B
FIG. 9C
FIG. 11A
FIG. 11B
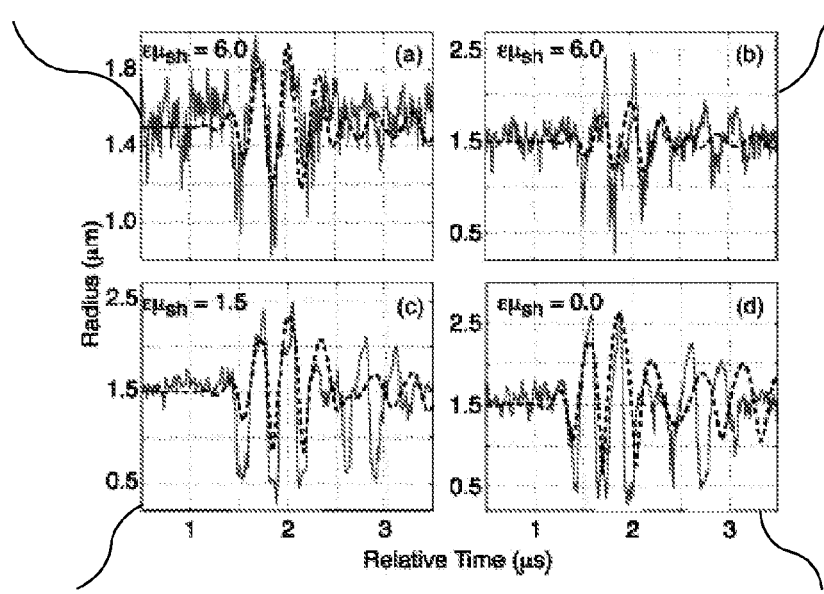
FIG. 11C
FIG. 11D TABLE III. Response curve parameters for evolving Optison® microbubble in an aqueous xanthan gum mixture. $P^-_{peak}$ is the measured peak negative pressure, $\epsilon\mu_{sh}$ is the fitted shell parameter, $R_0$ is the fitted ambient radius, and $R_{max}$ is the resultant maximum radius.

| Figure | $P^-_{peak}$ (kPa) | $\epsilon\mu_{sh}$ (nm Pa s) | $R_0$ (μm) | $R_{max}$ (μm) | $R_{max}/R_0$ |
|---|---|---|---|---|---|
| Fig. 11A | 340 | 6 | 1.50 | 1.93 | 1.29 |
| Fig. 11B | 340 | 6 | 1.50 | 1.93 | 1.29 |
| Fig. 11C | 340 | 1.5 | 1.50 | 2.33 | 1.55 |
| Fig. 11D | 340 | 0 | 1.50 | 2.61 | 1.68 |

FIG. 12

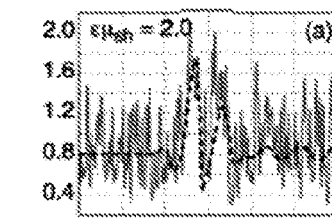

FIG. 13A

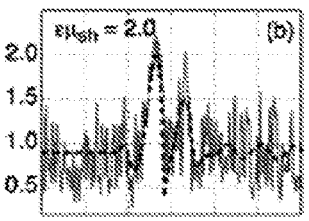

FIG. 13B

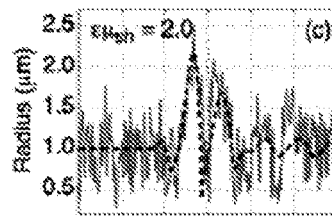

FIG. 13C

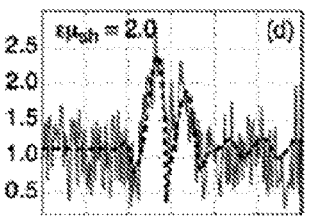

FIG. 13D

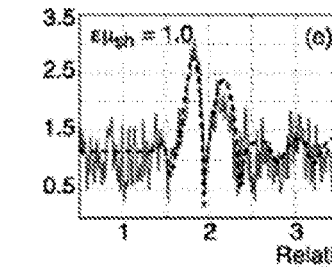

FIG. 13E

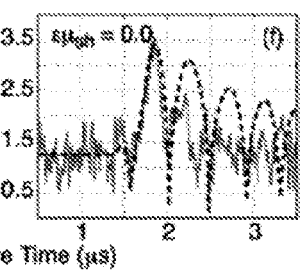

FIG. 13F

TABLE IV. Response curve parameters for evolving Sonazoid® microbubble in water. $P^-_{peak}$ is the measured peak negative pressure, $\epsilon\mu_{sh}$ is the fitted shell parameter, $R_0$ is the fitted ambient radius, and $R_{max}$ is the resultant maximum radius.

| Figure | $P^-_{peak}$ (kPa) | $\epsilon\mu_{sh}$ (nm Pa s) | $R_0$ ($\mu$m) | $R_{max}$ ($\mu$m) | $R_{max}/R_0$ |
|---|---|---|---|---|---|
| Fig. 13A | 390 | 2 | 0.80 | 1.74 | 2.18 |
| Fig. 13B | 390 | 2 | 0.90 | 1.99 | 2.21 |
| Fig. 13C | 390 | 2 | 1.00 | 2.19 | 2.19 |
| Fig. 13D | 390 | 2 | 1.10 | 2.38 | 2.16 |
| Fig. 13E | 390 | 1 | 1.15 | 2.77 | 2.41 |
| Fig. 13F | 390 | 0 | 1.25 | 3.42 | 2.74 |

*FIG. 14*

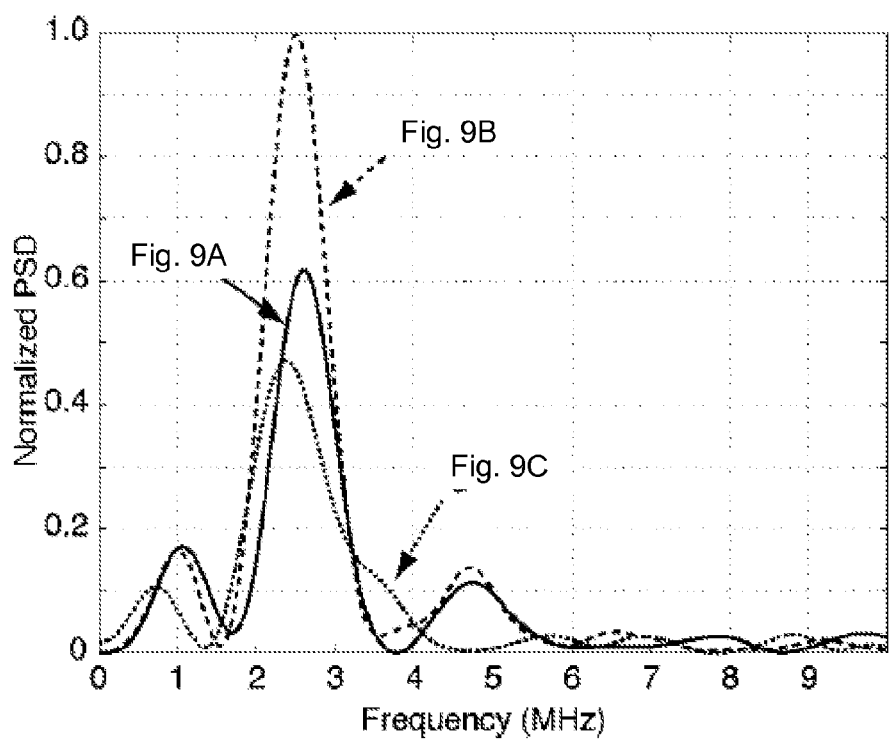

*FIG. 15*

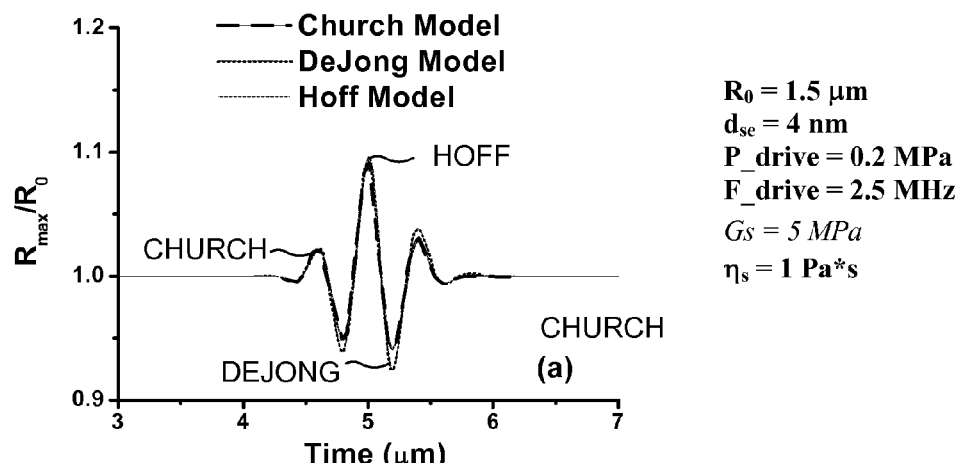
*FIG. 18A*
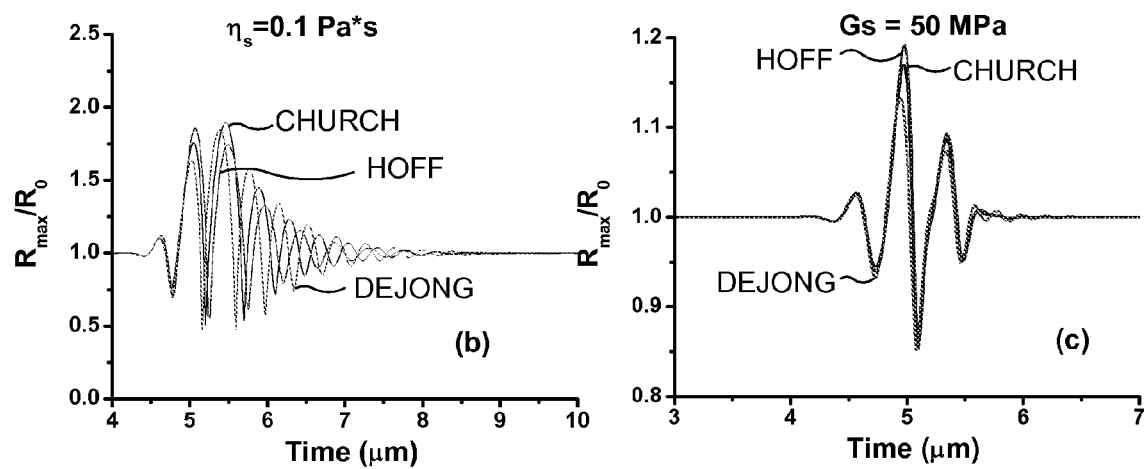
*FIG. 18B*  *FIG. 18C*

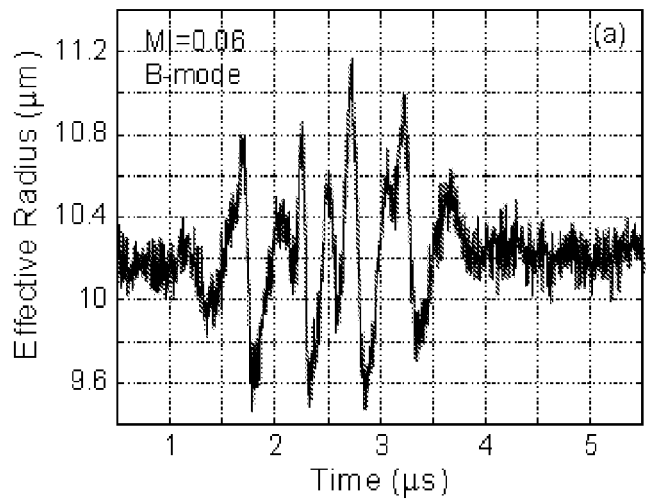
FIG. 26A
FIG. 26B
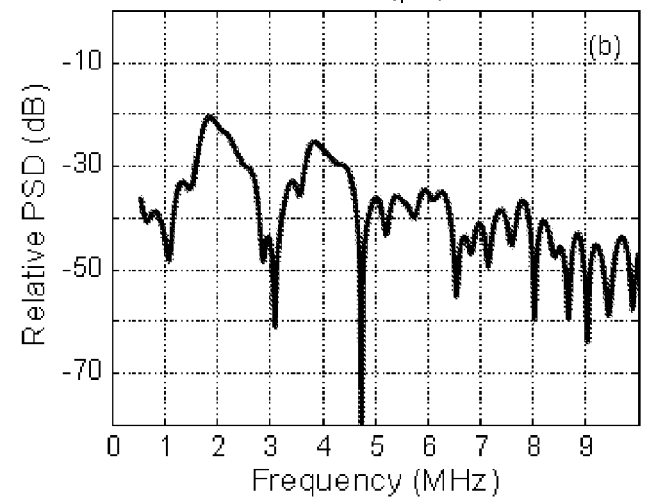
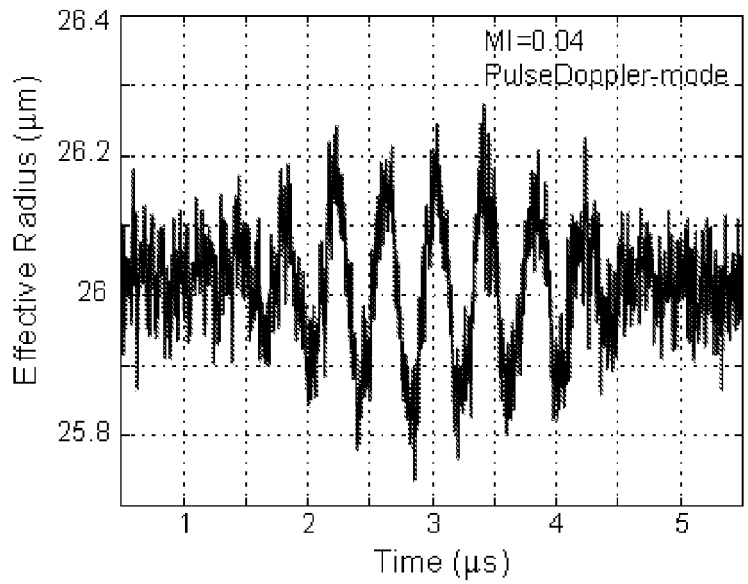
FIG. 27

USING OPTICAL SCATTERING TO MEASURE PROPERTIES OF ULTRASOUND CONTRAST AGENT SHELLS

RELATED APPLICATIONS

This application is based on a prior copending provisional application, Ser. No. 60/716,861, filed on Sep. 14, 2005, the benefit of the filing date of which is hereby claimed under 35 U.S.C. §119(e).

GOVERNMENT RIGHTS

This invention was made with U.S. Government support under grant No. EB0350-03 awarded by the National Institutes for Health (NIH). The U.S. Government has certain rights in the invention.

BACKGROUND

Gas-filled microbubbles with an encapsulating shell, generally referred to as ultrasound contrast agents (UCAs), are used regularly in diagnostic ultrasound, and are becoming important in therapeutic ultrasound applications. However, there is a need to better understand the physical interaction of ultrasound with UCAs, to enable UCAs to be more effectively used in diagnostic and therapeutic applications. Toward this goal, researchers have used acoustic scattering, attenuation, noise emission, and optical microscopy to study ultrasound/bubble interaction in connection with UCAs.

A basic characterization of UCAs typically involves measurement of their attenuation (scattering and absorption). These measurements provide information about the resonance frequency of the bubbles, and their damping. Some information about bubble populations can also be inferred from the measurements. However, there does not appear to be any correlation between attenuation and UCA performance or functionality. Broadband noise has also been used to obtain information about UCAs and their effect on the environment. Studies have found that a cavitation dose (a measure of initial cavitation activity) correlates very well with hemolysis (the destruction of red blood cells and associated release of hemoglobin) in vitro, suggesting that hemolysis can potentially be used as a measure of cavitational activity. Researchers have also compared the inertial cavitation thresholds of various UCAs by examining noise spectra, although thresholds obtained in this way are only indicative of relatively violent collapses, but not of less violent microbubble fragmentation mechanisms. Other research has shown how cavitational activity depends on pulse parameters in vivo, suggesting that optimal imaging is obtained when cavitation is reduced. As with attenuation measurements, noise emissions do not necessarily correlate with UCA performance or functionality.

A more direct approach to characterizing UCA performance involves determining acoustical backscattering, especially since diagnostic ultrasound is based on detecting backscattered signals. A variety of detection modalities have been used, including sub-harmonic, second-harmonic, and super-harmonic detection. In addition, various pulse schemes have increased the signal-to-noise ratio (SNR) of the acoustical data collection system. Such modalities, however, are limited because of a fundamental lack of understanding of the physics of ultrasound/microbubble interaction. For example, backscattering signatures are often machine dependent, or concentration dependent, but these dependencies are not well understood.

Recently, fundamental information about the interaction of ultrasound with UCAs has been obtained by using high-speed cameras. In these studies, single UCAs were insonified with pulses from a single element transducer, and the results were imaged with a camera, providing direct information about the response of the UCAs to the ultrasound. Although the image quality provided by high-speed cameras is excellent, and important information about bubble response and bubble destruction can be obtained in this manner, high-speed cameras are expensive, and the amount of data obtained are small. Usually only one, or at most, a few acoustic cycles of data can be collected, often requiring the splicing together of data from multiple experiments to achieve results that can yield the information being sought.

It would thus be desirable to provide approaches for investigating the physical properties of UCAs, particularly with respect to the properties of UCAs in the presence of ultrasound. The apparatus required to perform such investigations should be of modest expense.

SUMMARY

The concepts disclosed herein employ scattered light to measure the pulsations of a UCA as it is exposed to pressure variations (e.g., induced using ultrasound). In one exemplary embodiment, a UCA is placed in an imaging volume including either degassed water or a water/gel solution and is illuminated with a light source such as a laser. The UCA is exposed to pressure variations (preferably pulses of imaging or therapeutic ultrasound), while the optical scattering data are processed. The scattering intensity is related to the radius of the UCA. Thus, changes in the radius due to varying pressure conditions results in variations in the scattering intensity. The collected data are processed to provide a radius versus time (RT) relationship. The RT relationship is fit to one or more conventional dynamic models using known techniques (such as linear squares). Depending on the model employed, the fitted empirical data can be used to determine one or more UCA parameters, such as shear modulus, and shell viscosity.

Such a technique offers several advantages over imaging and acoustic techniques. Compared to high-speed optical imaging, the major advantage is in data collection; light scattering signals can be collected in real time, over tens, hundreds, and even thousands of acoustic pulses, providing the ability to monitor the evolution of UCAs with successive acoustic pulses. This technique is also relatively inexpensive (since a simple photomultiplier tube is used instead of an expensive high-speed camera). While the present technique alone cannot provide direct visual information regarding UCA dynamics and destruction as can be done in high-speed imaging, the present light scattering technique has advantages in being able to monitor the instantaneous motion of a microbubble.

A system for implementing the light scattering technique includes a fluid volume into which the UCA can be introduced, a light source for illuminating the UCA, a light sensitive detector for collecting light scattered by the UCA, a pressure source for varying the pressure in the fluid volume, a sensor for measuring actual pressure conditions, and a processor for manipulating the collected data. Preferably, the light source is a laser, the light sensitive detector is a photomultiplier tube (PMT), the pressure source is an imaging or therapeutic ultrasound probe/system, the sensor is a hydrophone, and the processor is a computing device (in one exemplary embodiment, an oscilloscope is used to manipulate the signal from the PMT before the data are processed by the computing device). The processor is configured to generate an RT curve based on the collected data, to fit the curve to one or more pre-defined models, and to calculate one or more parameters based on the fitted RT curve.

An exemplary method includes the steps of collecting scattering data using a system generally consistent with system described above, while a UCA is exposed to varying pressure conditions. An RT curve is generated based on the collected data, and the RT curve is fitted to one or more predefined models. The fitted curve is used to calculate one or more UCA parameters.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates exemplary method steps for using scattered light to calculate one or more UCA parameters;

FIG. 2 schematically illustrates an exemplary system for implementing the method steps of FIG. 1;

FIG. 3A graphically illustrates the relationship between scattering intensity and scattering angle;

FIG. 3B graphically illustrates the relationship between bubble radius and scattered light intensity;

FIG. 4A graphically illustrates a simulation for microbubbles with a varying shell parameter;

FIG. 4B graphically illustrates a waterfall plot of the simulated response curve R(t) for various initial bubble sizes and a fixed shell parameter using the same drive amplitude;

FIG. 4C graphically illustrates an exemplary simulation contour map of $(R_{max}-R_0)$ vs. $R_0$ and $\epsilon\mu_{sh}$;

FIG. 4D graphically illustrates the peak in the power spectral density (the main frequency component) of the simulation shown in FIG. 4A;

FIGS. 5A-5B, 6A-6B, and 7A-7B graphically illustrate empirical data and model fits for two different types of UCAs, in both water and a xanthan gum gel;

FIG. 8 (Table I) summarizes parameters for the data set corresponding to FIGS. 5A-5B, 6A-6B, and 7A-7B;

FIGS. 9A-9C graphically illustrate the slow evolution of a Sonazoid™ microbubble in water, collected using three successive groups of ten pulses;

FIG. 10 (Table II) summarizes parameters for the data set corresponding to FIGS. 9A-9C;

FIGS. 11A-11D graphically illustrate Optison™ response curves (i.e., RT curves) to individual (i.e., non-averaged) pressure pulses from diagnostic ultrasound in an aqueous/xanthan gum solution;

FIG. 12 (Table III) summarizes response curve parameters for the data set corresponding to FIGS. 11A-11D;

FIGS. 13A-13F graphically illustrate RT curves for optical scattering data collected from a Sonazoid™ bubble in water, showing individual responses (i.e., non-averaged responses) due to consecutive ultrasound pulses;

FIG. 14 (Table IV) summarizes response curve parameters for the data set corresponding to FIGS. 13A-13F;

FIG. 15 graphically illustrates normalized PSDs from FIGS. 9A-9C;

FIG. 16 schematically illustrates yet another exemplary system to collect light scattered by microbubbles during changing pressure conditions;

Figure 20A:
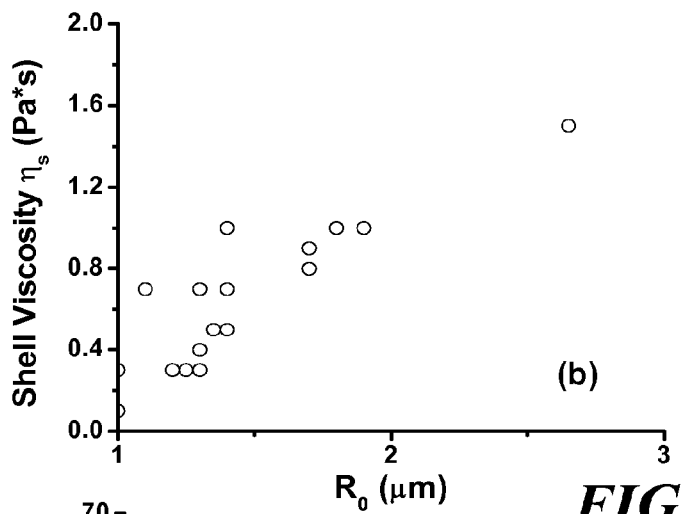
Figure 20B:
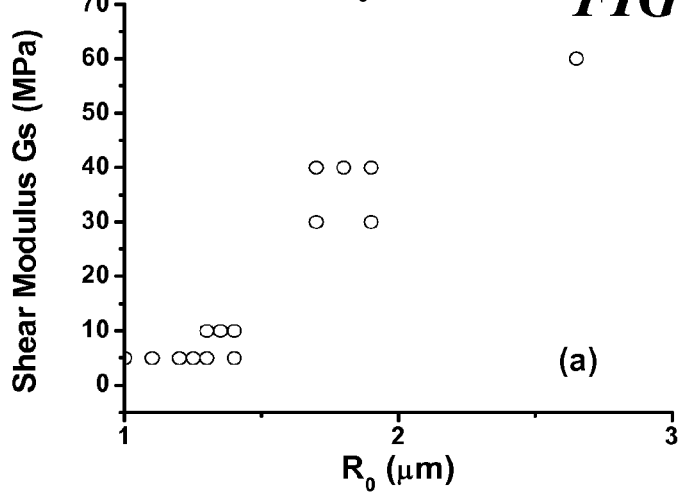
Figure 19A:
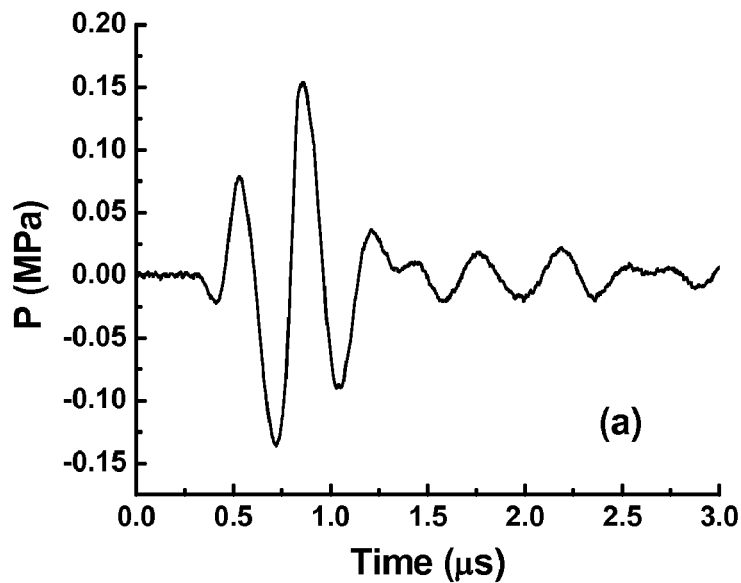
Figure 21A:
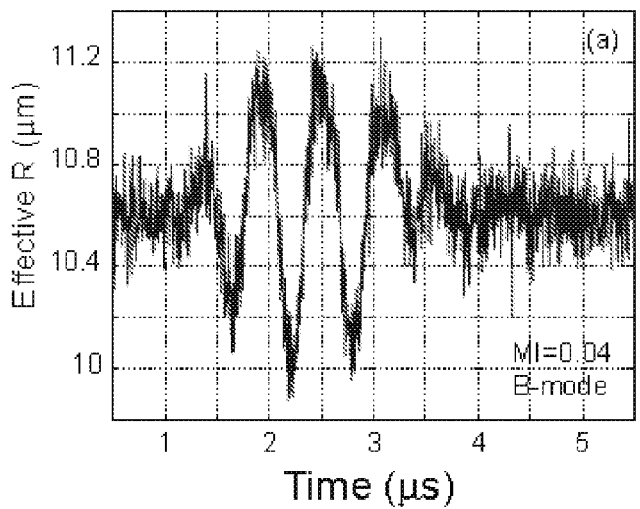
Figure 21B:
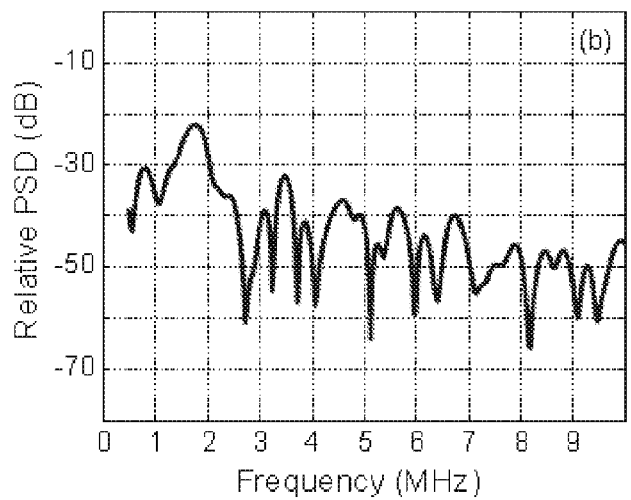
Figure 21C:
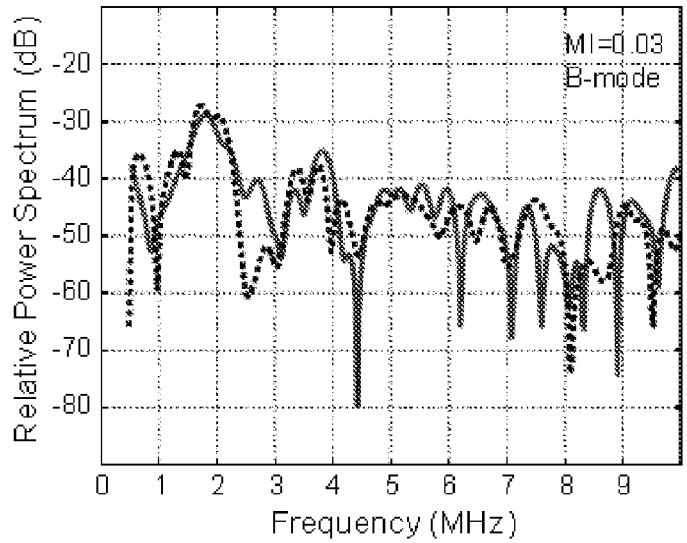
Figure 22:
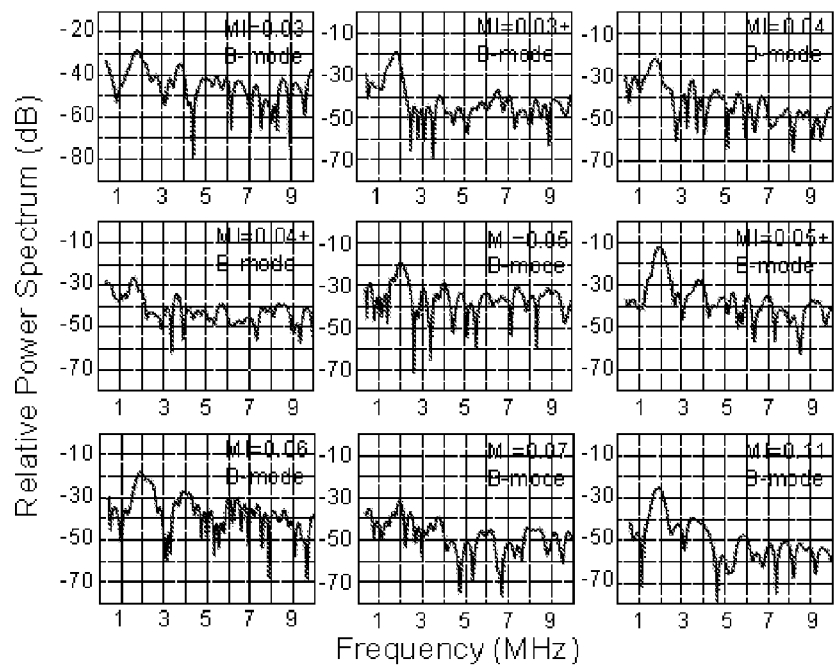
Figure 23A:
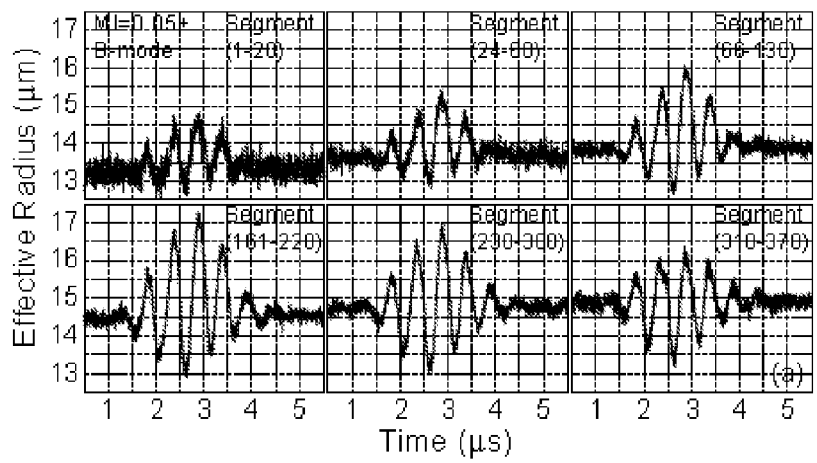
Figure 23B:
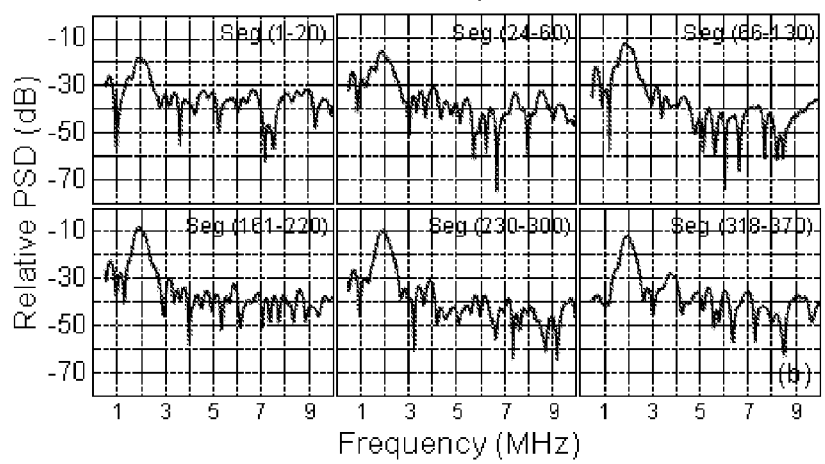
Figure 24:
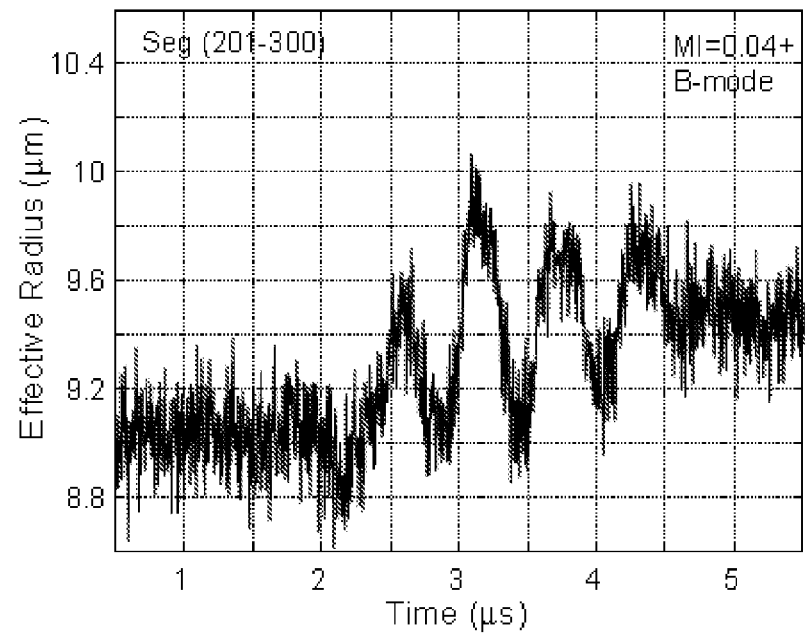
Figure 31:
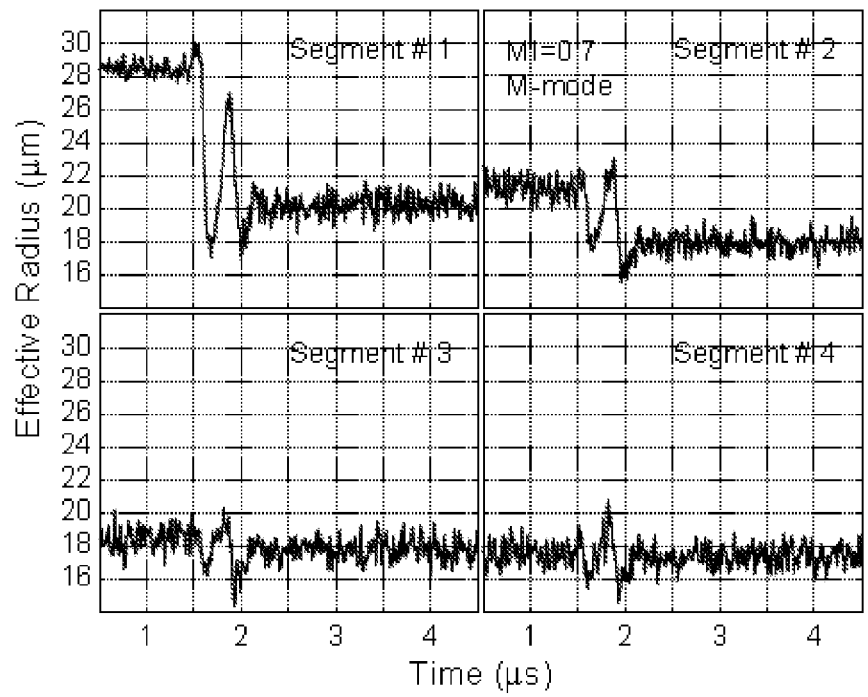
Figure 25A:
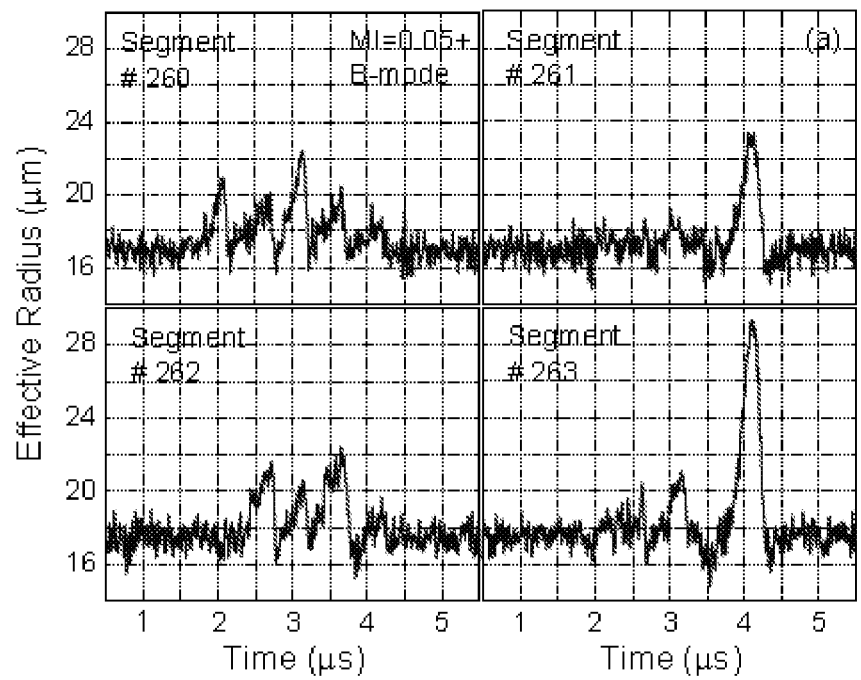
Figure 25B:
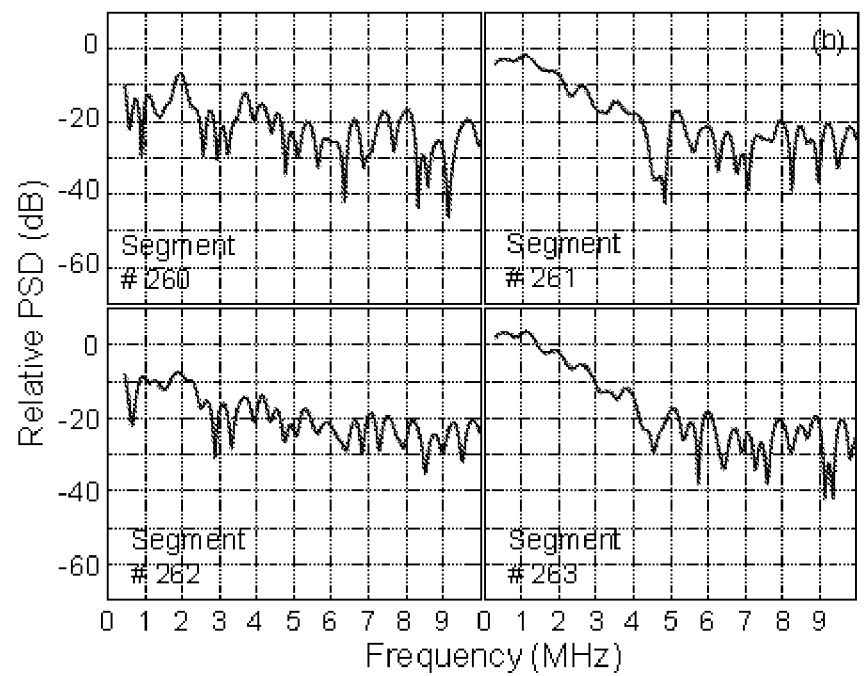
Figure 28:
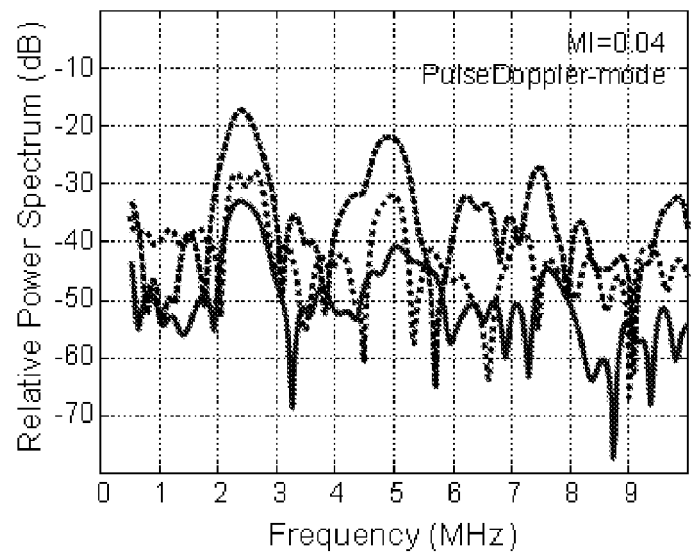
Figure 29:
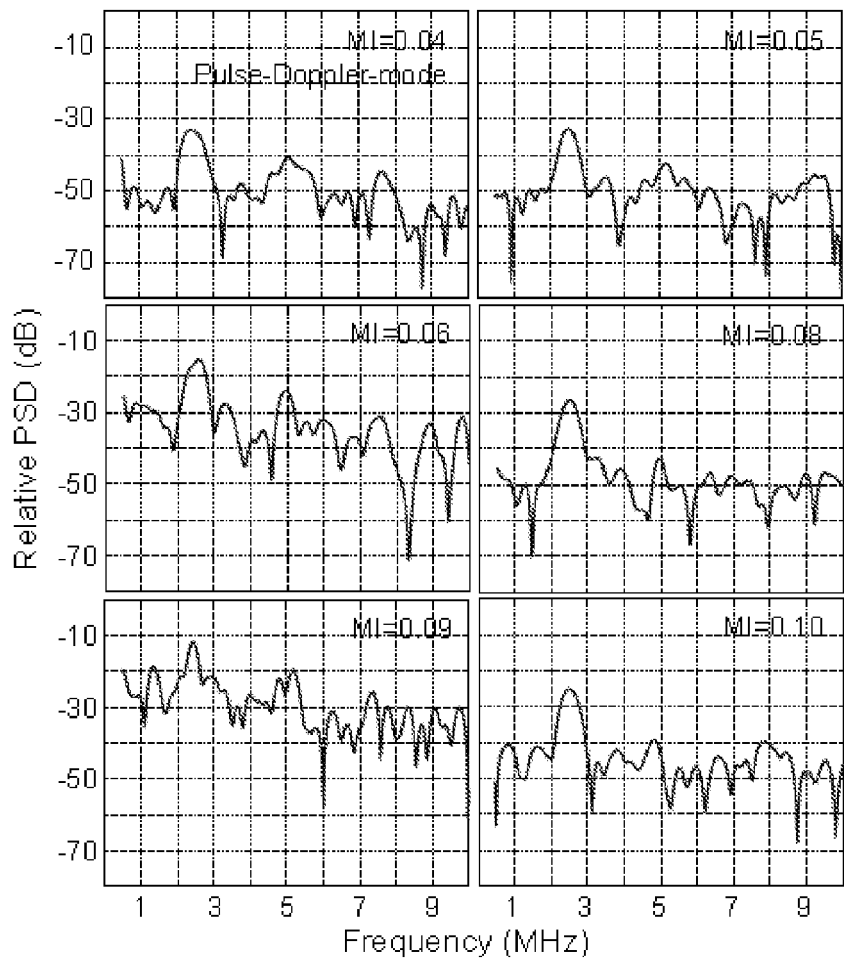
Figure 30A:
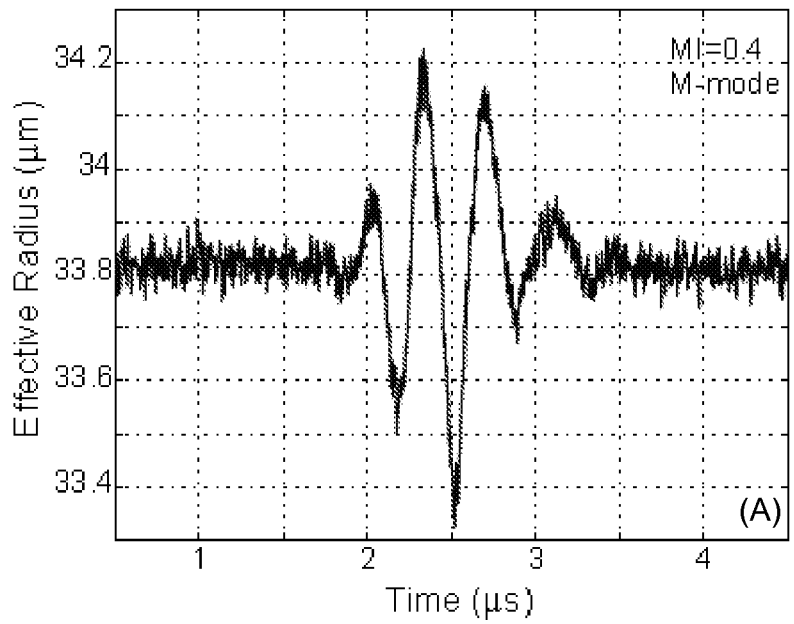
Figure 30B:
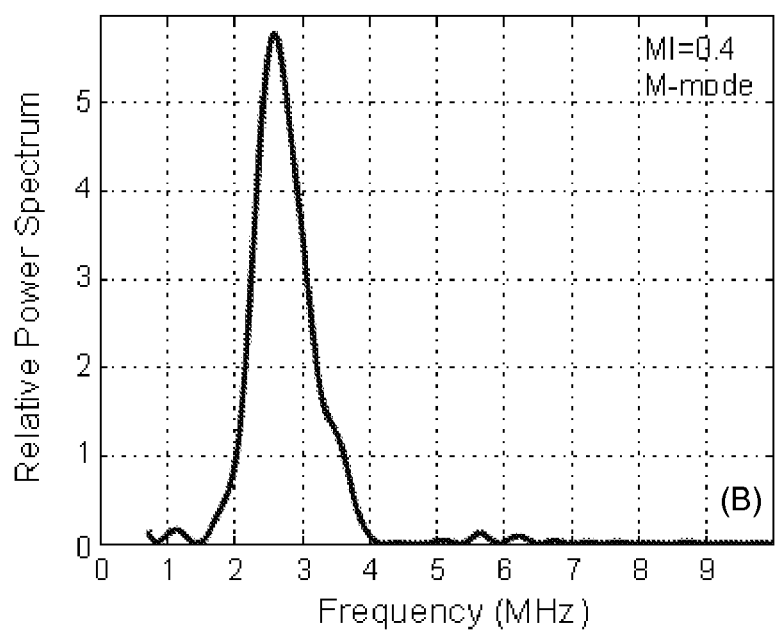

FIGS. 18A-18C graphically illustrate results provided by three different dynamic models, with varying parameters;

FIGS. 19A (showing measured driving pressure pulse) and 19B (showing measured bubble response and fits) graphically illustrate a comparison between the experimental data and simulated results, with a Sonovue™ bubble oscillating with a driving pressure amplitude of about 0.15 MPa;

FIG. 20A is a graph showing a change of a shell shear modulus as a function of radius;

FIG. 20B is a graph showing a change of a shell viscosity as a function of radius;

FIG. 21A graphically illustrates a typical effective RT curve of a group of UCA bubbles stimulated using B-Mode ultrasound;

FIG. 21B graphically illustrates the power spectrum corresponding to the data of FIG. 21A;

FIG. 21C graphically illustrates power spectrums collected from UCA bubbles collected at different times, using the same acoustic power settings;

FIG. 22 is a composite image graphically illustrating the power spectrum of UCA bubbles driven by different acoustic power settings using B-Mode ultrasound;

FIGS. 23A and 23B are composites images, with FIG. 23A including RT curves, and FIG. 23B including power spectrums;

FIG. 24 graphically illustrates data averaged over 100 consecutive pulses, showing changes to bubble size;

FIG. 25A includes RT curves of the same group of UCA bubbles during the consecutive insonification;

FIG. 25B shows power spectrums corresponding to the data of FIG. 25A;

FIG. 26A graphically illustrates an RT curve;

FIG. 26B graphically illustrates a power spectrum corresponding to the data of FIG. 26A;

FIG. 27 graphically illustrates a typical RT curve for a mass of UCA bubbles stimulated with Pulse-Doppler Mode ultrasound;

FIG. 28 graphically illustrates a power spectrum corresponding to the data of FIG. 27;

FIG. 29 is a composite image graphically illustrating the power spectrum of multiple UCA bubbles being driven by different acoustic powers (MI) in a Pulse-Doppler Mode;

FIG. 30A graphically illustrates a typical response from a mass of UCA bubbles stimulated by M-Mode ultrasound;

FIG. 30B graphically illustrates a power spectrum corresponding to the data of FIG. 30A; and FIG. 31 is a composite image that graphically illustrates consecutive effective RT curves of a mass of UCA bubbles responding to M-Mode stimulation.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

As used herein and the claims that follow, it should be understood that the terms "UCA," "microbubble," and "encapsulated microbubble" have been used interchangeably. These terms refer to relatively small (on the order of microns in size) bubbles including a shell and a core. Shells are generally implemented using lipids, polymers, and/or albumin (although such materials are intended to be exemplary, rather than limiting), while cores are generally implemented using gases such as air, perfluoropropane (PFP), perfluorobutane (PFB), and octafluoropropane (OFP) (although such materials are intended to be exemplary, rather than limiting).

Figure 1:
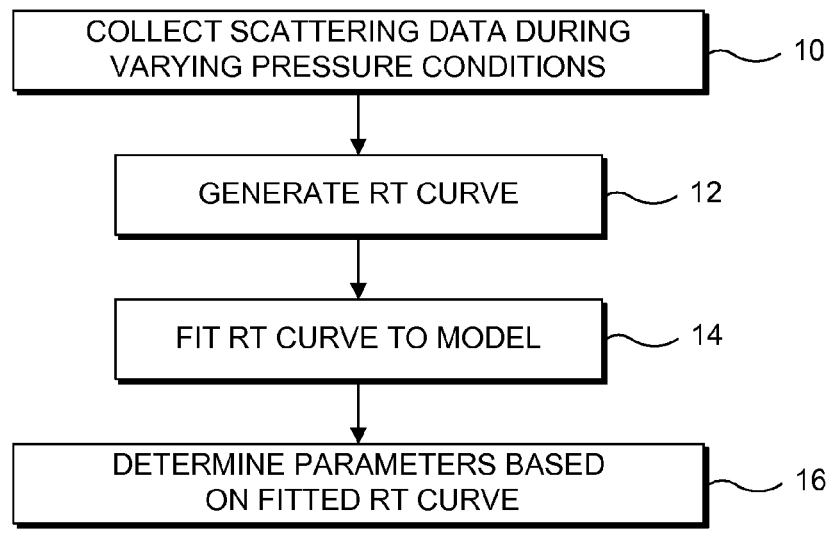

FIG. 1 schematically illustrates exemplary method steps for using scattered light to calculate one or more UCA parameters. The exemplary method steps include collecting light scattered from a UCA while the UCA is exposed to varying pressure conditions, as indicated by a block 10. An RT curve is generated based on the collected data, as indicated by a block 12, and the RT curve is fitted to one or more predefined models, as indicated by a block 14. The fitted curve is used to calculate one or more UCA parameters, as indicated in a block 16.

Figure 2:
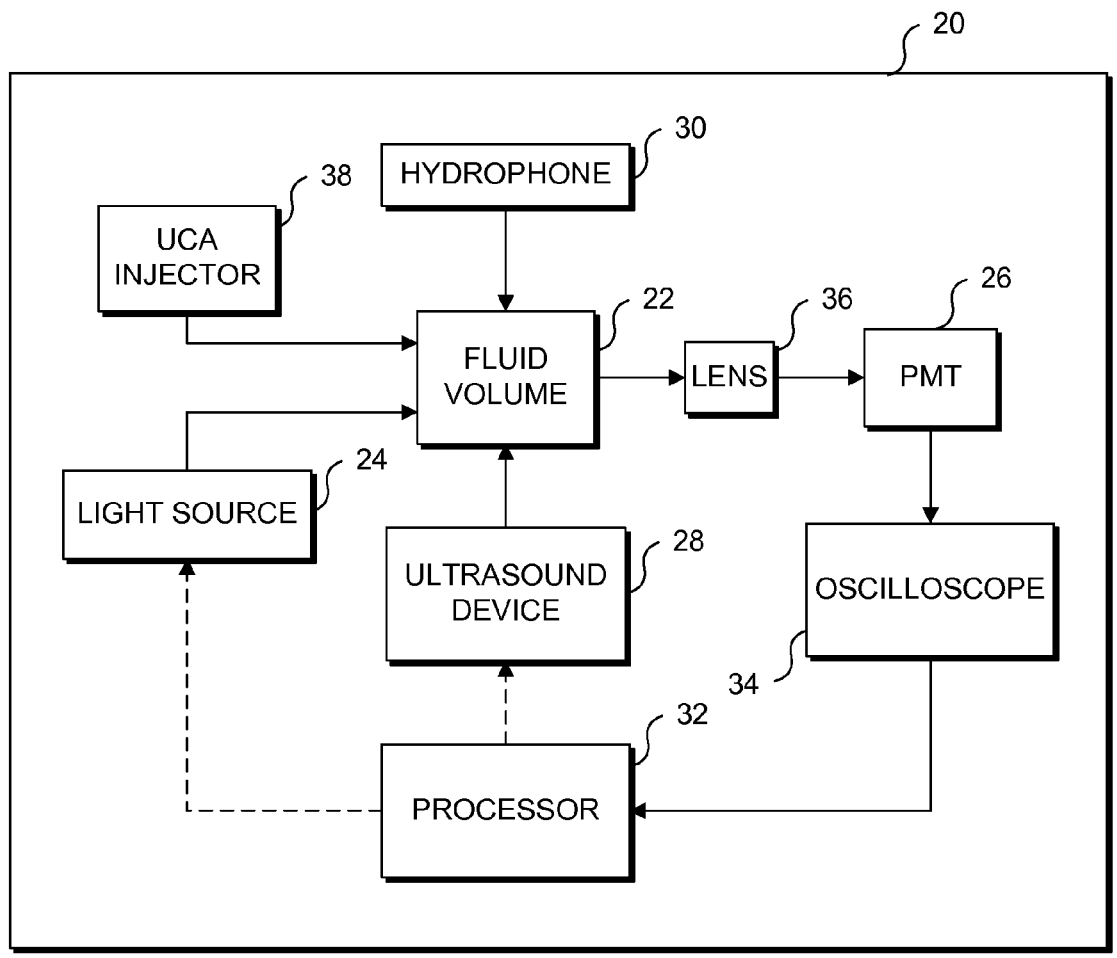

FIG. 2 schematically illustrates an exemplary system 20 for implementing the method steps of FIG. 1. System 20 includes a fluid volume 22 (for example, implemented using an optically transparent container, such as glass or plastic) into which the UCA can be introduced, a light source 24 for illuminating the UCA, a light sensitive detector 26 for collecting light scattered by the UCA, a pressure source for varying the pressure in the fluid volume (preferably implemented using an ultrasound probe/system 28), a sensor 30 for measuring actual pressure conditions, and a processor 32 for manipulating the collected data. In this exemplary embodiment, light source 24 is a laser, light sensitive detector 26 is a photomultiplier tube (PMT), sensor 30 is a hydrophone, and processor 32 is a computing device (an oscilloscope 34 can be used to manipulate the signal from the PMT before the data are processed by the computing device). Processor 32 is configured to generate an RT curve based on the collected data, to fit the curve to one or more pre-defined models, and to calculate one or more parameters based on the fitted RT curve. A lens 36 may (or may not) be used to direct light scattered by a UCA in the fluid volume toward the PMT. A UCA injector 38 (such as a syringe pump or pipette) is used to inject a UCA agent into the fluid volume. While not specifically shown in the Figure, a scattering angle from about 70 degrees to about 90 degrees is desirable, and the relative orientations of one or more of the injector, light source, and lens can be manipulated to achieve such a scattering angle. The laser light source employed in an empirical system was a red helium/neon (HeNe) laser, having a wavelength of 633 nm.

Various Figures provided herein graphically depict RT curves generated using light scattered by microbubbles. Such Figures often include both solid lines and dashed lines. Except where otherwise indicated, the solid line refers to empirically collected data, while the dashed line refers to fitted data. Those of ordinary skill in the art will readily recognize that many fitting algorithms and commercial fitting software programs are available. It should also be recognized that many different dynamic models describing microbubble are available, or may become available. Many variables in the model can be measured or estimated, to minimize the number of variables that are fitted. The unknown variables can be limited to shell parameters. Examples of variables that can be measured include pressure (e.g., as measured by the hydrophone) and bubble radius (which can be measured optically using a microscope or microscope and camera, or with light scattering while the bubble is static). Radius measurements for many UCAs are readily available in the published literature.

Having briefly discussed the exemplary method and apparatus, it will be useful to provide general information about light scattering and dynamic models describing the motion of microbubbles, so that the above noted concepts are understood in context.

Figure 3A:
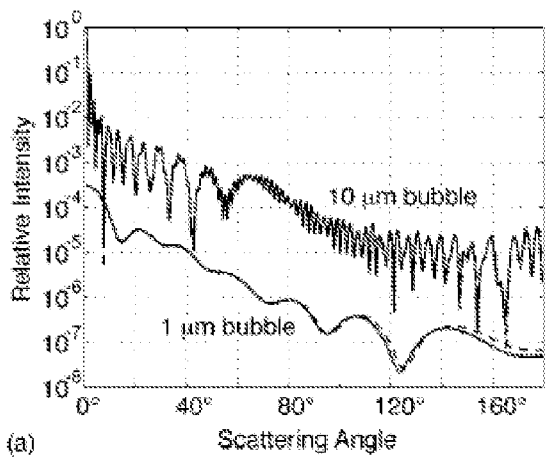
Figure 3B:
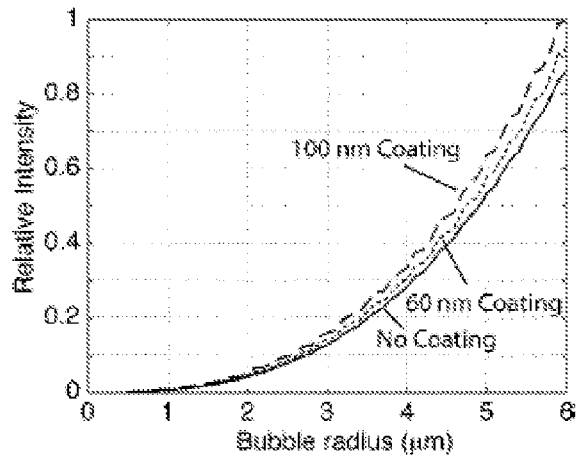

The Mie theory describes light scattering from homogeneous spheres (or bubbles, in the context of the current disclosure) in a homogeneous environment. In general, this theory indicates that the intensity of scattered light depends strongly on the observation angle. For an air bubble in water, and for a single light detector, the observation angle should be near the critical angle (about 83 degrees) from forward scattering. This preference is based on a physical-optics approximation, which suggests that the scattered light intensity is a monotonic function of bubble size. Calculations and empirical data have indicated the presence of relatively thin shells (i.e., on the order of 10-15 nm), which does not substantially change the relationship between scattering intensity and scattering angle (graphically illustrated in FIG. 3A, where the dashed lines represented thin shell bubbles and the solid lines representing bubbles without shells are nearly indistinguishable), indicating the Mie theory can be usefully applied to UCA (which are not homogenous spheres), as well as to homogeneous spheres. Significantly, the Mie theory also establishes a monotonic relationship between sphere/bubble size and scattered light intensity (larger bubbles result in an increase in the intensity of the scattered light), as indicated in FIG. 3B. Because of the relationship indicated in FIG. 3B, it is straightforward to convert scattered light intensity into a radius. Significantly, even if the calculated radius varies from the actual radius, the relative differences between radii calculated based on different measured scattered light intensities can still be quite useful in generating the RT curve discussed above, which once fitted to a selected dynamic bubble model, enables calculation of UCA parameters to be carried out, generally as discussed above.

With respect to the system of FIG. 2, it is important to recognize that the detector collects light from a finite angular distribution, not just at a single angle (the lens being employed to increase the light intensity onto the detector). Preferably, the angular span ranges from approximately 70° to 90°. The curve in FIG. 3B shows the relative integrated intensity over this span as a function of bubble size.

As noted above, the use of dynamic models of UCA bubbles is an important aspect to the concepts disclosed herein. Fortunately, there are many models from which to choose, and empirical evidence suggests that the concepts disclosed herein can be used with many of these models. There are several approaches for modeling a coated bubble, many of which are based on the RPNNP equation, which describes the response of a spherical bubble to a time-varying pressure field (including acoustic pressure) in an incompressible liquid:

$$\rho_L R \ddot{R} + \frac{3}{2} \rho_L \dot{R}^2 = P_g \left( \frac{R_0}{R} \right)^{3\gamma} + P_v - P_0 - \frac{2\sigma}{R} - \delta \omega \rho_L R \dot{R} - P_a(\omega t) \quad (1)$$

where $R_0$ is the initial bubble radius, $\rho_L$ is the density of a Newtonian liquid, $P_0$ is the ambient pressure, $P_v$ is the vapor pressure, $\sigma$ is the surface tension, $\gamma$ is the polytropic exponent of the gas, $\delta$ is the damping coefficient, $P_a$ is the amplitude of the incident acoustic pressure, ω is the angular frequency of driving signal, and $P_g$ is the gas pressure inside the bubble ($P_g=P_0-P_v+2\sigma/R_0$).

The assumptions for Eq. (1) include following: (1) the motion of the bubble is symmetric; (2) the wavelength of ultrasound is much larger than the bubble radius; (3) no rectified diffusion occurs; and, (4) the bubble contains gas or vapor, which is compressed and behaves according to the gas law, with the polytropic parameter held constant.

De Jong's model, Church's model, Hoff's model, and Sarkar's model, discussed in greater detail below, are each modified from the general PRNNP equation. The choice of which bubble dynamics model is employed is not based on the relative accuracy of any particular model. It should be recognized that these models should not be considered restrictive; as new models that may be developed can also be employed.

Initial work in developing the concepts disclosed herein employed a simplified model that has previously been used in comparisons with high-speed camera images of encapsulated microbubble dynamics, the Morgan et al model. A major advantage in the Morgan model is that it has a reduced set of fitting parameters. The Morgan model is:

$$\rho R\ddot{R} + \frac{3}{2}\rho\dot{R}^2 = \left(P_0 + \frac{2\sigma}{R_0} + \frac{2\chi}{R_0}\right)\left(\frac{R_0}{R}\right)^{3\gamma}\left(1-3\frac{\dot{R}}{c}\right) - \frac{4\mu\dot{R}}{R} - \frac{2\sigma}{R}\left(1-\frac{\dot{R}}{c}\right) - \frac{2\chi}{R}\left(\frac{R_0}{R}\right)^2\left(1-3\frac{\dot{R}}{c}\right) - 12\varepsilon\mu_{sh}\frac{\dot{R}}{R(R-\varepsilon)} - (P_0 + P_{drive}(t)) \quad (2)$$

where R is radius of the bubble, $R_0$ is initial radius of the bubble, $P_0=1.01\times10^5$ Pa is the ambient pressure, $P_{drive}(t)$ is the acoustic driving pressure, p=1000 kg/m³ is the liquid density, γ≈1 is the ratio of specific heats, c=1500 m/s is the sound speed in the liquid, σ=0.051 N/m² is the surface tension coefficient, χ=0 is the shell elasticity, μ=0.001 Pa s is fluid shear viscosity, $\mu_{sh}$ is the UCA shell shear viscosity, and ε is the UCA shell thickness.

Using Eq. (2), the relevant parameter space was examined to determine the relationship between the various parameters, which was done in order to determine if a fit to the data would be unique. For UCAs, this parameter space covers $0.1 \leq R_0 \leq 6$ mm, $0 \leq \varepsilon\mu_{sh} \leq 8$ nm Pa s, and $0.0235 \leq P_{drive}(t) \leq 1.2$ MPa (peak negative), relevant for thin shelled agents. Because isothermal behavior is assumed, the elasticity terms cancel. Assuming R>>ε (also assumed by Morgan in developing the model), the only term with shell parameters is given by $12\varepsilon\mu_{sh}\dot{R}/R^2$. Hence, the shell parameter can be referred to as the product $\varepsilon\mu_{sh}$. Note that there are initially three unknowns: $R_0$, $P_{drive}(t)$, and the product $\varepsilon\mu_{sh}$.

Referring to the driving pressure $P_{drive}(t)$, a calibrated needle hydrophone (the sensor in FIG. 2) can be used to measure acoustic driving pressure, as an input to the Morgan bubble dynamics model, thereby decreasing the unknowns by one. Most of the initially collected empirical data was obtained from the M-Mode of a diagnostic ultrasound system (the ATL Ultramark 4Plus™). Empirical data indicate the acoustic driving pressure of the selected ultrasound system falls well within the above-noted parameter space for the driving pressure.

The remaining parameters are $R_0$ and the product $\varepsilon\mu_{sh}$. Significantly, examining the parameter space is necessary in order to ensure that the empirically fitted data will be unique.

Figure 4A:
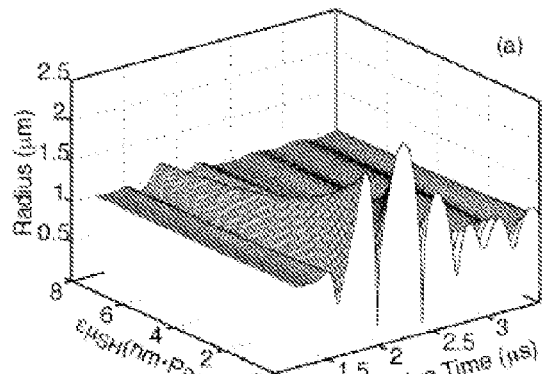
Figure 4B:
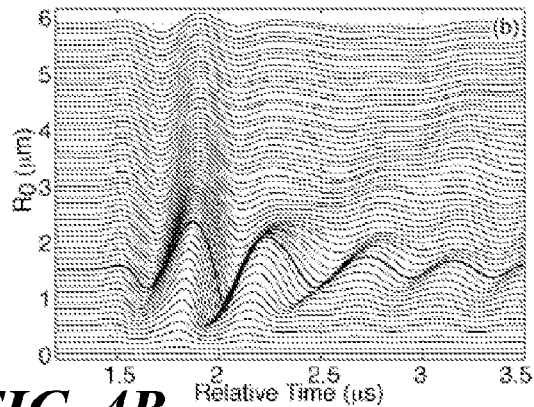
Figure 4C:
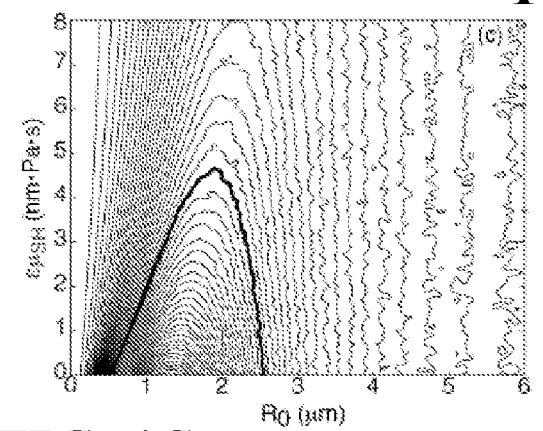

FIG. 4A graphically illustrates a simulation for microbubbles with a varying shell parameter, for an initial bubble radius size of $R_0=1$ μm, and $P_{drive}(t)=235$ kPa peak negative pressure. FIG. 4B graphically illustrates a waterfall plot of the simulated response curve R(t) for various initial bubble sizes and a fixed shell parameter (same drive amplitude). The resonant bubble size is darkened. FIG. 4C graphically illustrates a simulation contour map of ($R_{max}-R_0$) vs. $R_0$ and $\varepsilon\mu_{sh}$ (with the same drive amplitude). Finally, FIG. 4D graphically illustrates the peak in the power spectral density (the main frequency component) of the simulation in FIG. 4A. Significantly, the resonant bubble size can be seen in FIG. 4B, where the curves appear to bunch together. As expected, the response curve R(t) has significant fluctuations near resonance. In FIG. 4C, the resonant bubble size increases with increasing shell parameter, from about 1.3 μm to about 2.1 μm, which is an expected behavior, consistent with the thin shell behaving as a damping mechanism. That is, an increase in damping results in a decrease in resonant frequency, or, equivalently, an increase in resonant size. FIG. 4C also shows that near resonance, there is a strong dependence on the shell parameter (when moving from contour to contour). However, for bubbles larger than about 3 μm, the dependence is weak at best (note the vertical contour lines). Thus, for larger UCAs, this model would not be useful for fitting shell parameters to the data.

Furthermore, the maximum amplitudes of the two main peaks in FIG. 4A change relative to each other as the shell parameter increases. The first peak, initially smaller than the second peak, becomes the larger peak for $\varepsilon\mu_{sh}>0.4$ nm Pa s, which is most probably a consequence of the specific pressure pulse used. That is, the pressure pulse has two resonant peaks, near 2.3 MHz and 3.2 MHz. Because the resonance size depends on the shell parameter, as the shell parameter increases, it is possible that first one, and then the other of these resonances are manifest, resulting in a change in the bubble response.

Figure 4D:
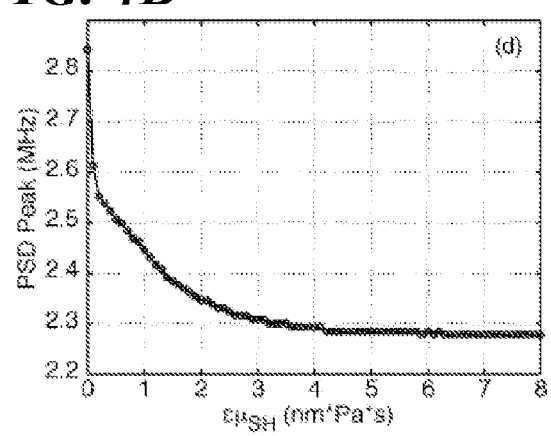

The power spectral density (PSD) for the example of FIG. 4A is shown in FIG. 4D. The peak in the PSD decreases with increasing shell parameter, but levels off quickly. It would be difficult to distinguish between two bubbles with different shell parameters, for $\varepsilon\mu_{sh}>3$ nm Pa s, using only the PSD; however, the PSD might be used to determine when the shell breaks. The PSD is the frequency response of the system driven by the measured pressure pulse, and thus, includes the spectral characteristics of the driving pulse. It is nevertheless instructive to compare it to the bubble's resonance frequency, obtained from linearizing the equation of motion, setting $R \to R_0(1+\epsilon)$, expanding relevant terms in a binomial expansion, and neglecting second-order and higher terms. This leads to the frequency of oscillation, $f_r$, as follows:

$$f_r = \frac{1}{2\pi}\sqrt{\frac{3\gamma}{\rho R_0^2}\left(P_0 + \frac{2\sigma}{R_0} + \frac{2\chi}{R_0}\right) - \frac{2\sigma+6\chi}{\rho R_0^3} - \frac{(4\mu+12\varepsilon\mu_{sh}/R_0)^2}{\rho^2 R_0^4}} \quad (3)$$

Using the parameters above ($R_0=1$ μm, γ=1), and considering the undamped case ($\varepsilon\mu_{sh}=\mu=0$), the linear resonance frequency, $f_r$, is approximately 3.5 MHz. The frequency of oscillation does not follow the PSD curve (because the PSD includes the driving pulse spectral characteristics). Instead, it drops quickly to zero near $\varepsilon\mu_{sh}=1.6$ nm Pa s (for a 1 μm bubble), which appears to imply that smaller bubbles are over damped and do not resonate.

The discussion above has been limited to resonances and the relationship with a particular pressure pulse. However, the most important reason for mapping the parameter space is to determine if a solution is unique, because as mentioned above, there are two unknown parameters to be fitted, namely $R_0$ and the product $\epsilon\mu_{sh}$. To help solve this problem, it is helpful to focus on FIG. 4C (the contours of $(R_{max}-R_0)$ vs. $R_0$ and $\epsilon\mu_{sh}$), bearing in mind that the pressure amplitude has been measured, which constrains the analysis to the amplitude of $R(t)$.

If $R_0 > 3$ μm, the quantity $(R_{max}-R_0)$ is not as sensitive to the shell parameter, making unique fits difficult. Fortunately, with UCAs, the majority of bubbles are in the size range from about $R_0=1$ μm to about 2.5 μm. In this range, the contours show sensitive dependences (note the darkened contour line in FIG. 4C). If product $\epsilon\mu_{sh}$ is initially set to 2 nm Pa s, there will be two possible solutions for $R_0$ that would result in the same $(R_{max}-R_0)$ value, near 1 μm and 2.4 μm. However, $R_{max}$ itself is different for these two values. For example, if the condition $R_0=1$ μm is chosen, then $R_{max}=1.6$ μm, and if $R_0=2.4$ μm, then $R_{max}=3.0$ μm. The empirical data will constrain the results to only one of these values. In conclusion, although the above discussion leads to a two-parameter fit, the data constrain the solutions to a single parameter. In this model, the shell parameter is not important for larger bubbles, but for microbubbles of interest, it is a sensitive parameter; thus, the task of uniquely fitting the data to the model is feasible.

The following empirical study employed a system generally consistent with that shown in FIG. 2. The study involved injecting individual microbubbles into a region of interest, insonifying the microbubble with ultrasound, and collecting light scattered from the microbubble. The region of interest is the small volume of liquid where the ultrasound and laser illumination intersect a microbubble. For most studies, the liquid was filtered (0.2 μm porosity) and de-ionized (having >18 MΩ resistance) water.

Two methods were used to inject UCAs into the region of interest. Most often, a highly-diluted UCA solution (calculated to be on the order of $10^5$/ml) was injected into a rectangular water tank (3.5 cm² cross section, filled to a height of about 4 cm) with a syringe pump (at a rate of 10 ml/h) with a 0.5 mm inner-diameter tube. The ejection of the microbubble was approximately one-half cm from the laser beam path. Based on the numbers given above, it might be expected that subsequent bubbles would generate a scattering "event" about every 3 ms. However, the actual frequency of events was much less (approximately one event over several seconds). The most likely reason for this phenomenon is due to UCA congregation within the syringe, and at curves in the tubing, especially where the tubing goes up and over a lip. Also, bubbles ejected from the tip may move away from the laser beam, and not into it.

To verify that the measured response curves were for single microbubbles, UCAs were injected manually into the water-filled vessel that contained a small amount of a water soluble gum (e.g., xanthan gum). The xanthan gum increased the viscosity of the liquid slightly, so that after injection, the microbubble came to rest and remained relatively stationary. The microbubble was then imaged with a back-lit LED, microscope, and CCD camera to verify that there was indeed a single bubble in the region of interest. The fluid vessel was then repositioned so that the bubble was at the center of the laser beam/ultrasound probe focus. Empirical data indicate that there was no major difference in measurements between experiments conducted in water and the xanthan gum mixtures, except that the added xanthan gum yielded higher noise levels.

The xanthan gum gel preparation was performed as follows: 2.6 grams BT food grade xanthan gum powder, 12 g glycol, and 600 g water (slightly degassed) were combined. First, the powder and glycol were mixed and poured into a beaker, and the water was then poured into the beaker very slowly over a stick to minimize the trapping of bubbles. The mixture was stirred slowly for up to an hour using a magnetic stir bar to make it homogeneous. The gel was finally poured slowly into the experimentation vessel. Because of the possibilities of contamination and bacterial growth, a new gel was made prior to the start of each experiment. If more viscous gels are used, removing trapped bubbles becomes much more difficult and requires centrifuging the solution for up to 3 hours.

In the empirical study, a 30 mW HeNe laser was employed as the light source to illuminate the microbubbles. With a lens, the beam waist at the region of interest (i.e., where the microbubble, the laser beam, and the ultrasound intersect) was focused to less than 100 μm (although, because some scattering occurs through the plastic water tank and through the water, it is difficult to accurately measure the beam waist). The light scattered from the bubble was then focused with a 5 cm lens onto a PMT detector (Hamamatsu, Model 2027™). The main function of the collecting lens was to increase the signal/noise (covering the angles 70°-90°). The PMT was biased at 21000 V. A HeNe line filter was placed against the PMT cathode window to block other sources of light. The output of the PMT was conveyed directly to a high-speed digital oscilloscope (LeCroy), and then to a personal computer for post-processing. As noted above, the varying pressure conditions were supplied using an imaging ultrasound probe (placed directly in the fluid vessel, although an externally disposed transducer can also be employed, so long as the fluid vessel wall is acoustically transparent).

Data collection was performed in a sequence mode, where high-resolution data files are collected during each ultrasound pulse. The total data collected are limited by the available memory of the oscilloscope. For the empirical study, data sequence records of 40 consecutive acoustic pulses were collected before transferring the file to the computing device. Each segment included a 5 ms long window, with a resolution of 4 ns. The segments were separated by about 1 ms (triggered by the source transducer). Appropriate delays in triggering were used to ensure that the bubble response was centered in the segment window.

The imaging ultrasound probe (the Ultramark 4Plus™) was operated in the M-Mode at about 1 kHz pulse repetition frequency (PRF). A calibrated needle hydrophone monitored the acoustic pressure. In actual experiments, the hydrophone was placed at an angle relative to the pulse. Thus, the relative angle between the transducer and hydrophone had to be measured, and then a separate water tank was used to determine the hydrophone response as a function of the angle of the ultrasound probe. This hydrophone response as a function of the angle, expressed as a multiplicative factor, was then used in all subsequent data analyses.

Other empirical studies employed a single element high intensity transducer, which was inserted through the bottom of the vessel, with the hydrophone being positioned directly above it, so that the angle problem described above was not an issue. For this configuration, relevant transducer parameters are center frequency f=1.8 MHz, focal length=63 mm, −6 dB for a bandwidth=500 kHz, 2.5 cm active area, 10 cycle bursts, and 10 kHz PRF.

FIGS. 5A-5B, 6A-6C, and 7A-7D graphically illustrate data and model fits for Optison™ and Sonazoid™ UCAs, in water and diluted aqueous xanthan gum gel. There are two important points to note. First, the light scattering model and data both produce an intensity versus time I(t) that must be converted to a radius versus time R(t). For the experimental data, the scattered intensity is found by subtracting the background intensity from the total intensity. The model generates a relative value, so a multiplicative scaling factor must be found to match the model to the data. Once the scaling factor is found, it is unchanged for all subsequent experiments. The relationship described above for FIG. 3B can be used to convert the relative intensity to a radius. A second point to note is that best fit studies were required in order to constrain the two unknowns ($R_0$ and the product $\epsilon\mu_{sh}$). As described above, the expected ranges for the parameters were defined. Within these ranges, it was determined that a deviation of about 65% in $R_0$ would generate a good fit. In addition, it was determined that shell parameter values published in the literature would enable good fits to be achieved. Therefore, for these studies the initial shell parameter for Optison™ was defined as $\epsilon\mu_{sh}$=6.0 nm Pa s, and for Sonazoid™, the initial shell parameter was defined as $\epsilon\mu_{sh}$=2.0 nm Pa s. Deviations of up to about ±1 nm Pa s also generated good fits. It was determined that UCA oscillations from pulse to pulse were relatively regular, so several pulses were grouped together to improve the SNR.

Figure 5A:
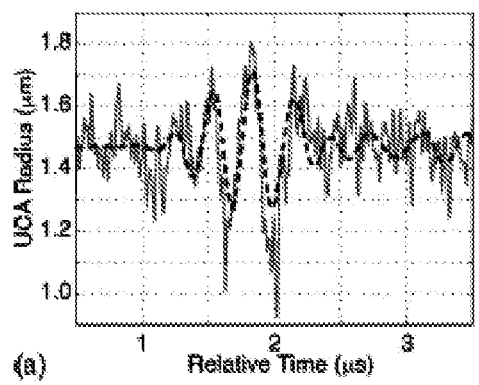
Figure 5B:
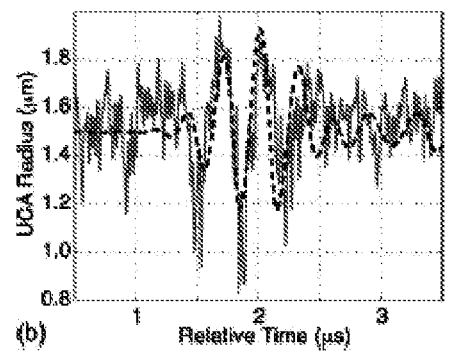

FIG. 5A graphically illustrates an RT curve generated using an Optison™ UCA pulsed with the Ultramark 4Plus™ in water, while FIG. 5B graphically illustrates an RT curve generated using an Optison™ UCA pulsed with the Ultramark 4Plus™ in the water/xanthan gum solution. For each RT, ten consecutive pulses (segments) were averaged together to increase the SNR. The measured peak negative pressure and fitted initial bubble radius are 210 kPa and 1.47 µm, respectively. For these parameters, the data and simulations exhibit quasi-linear motion. For these and other data, very good agreement with the major oscillations is obtained. The smaller ring-down oscillations are more difficult to fit because of the lower signal strength. Although the Morgan model discussed above is arguably not the most accurate model to use for encapsulated microbubbles, the overall good fit to the data suggests that the empirical data is indeed based on measuring the pulsations of individual encapsulated microbubbles. To provide verification that the light scattering was being performed on single bubbles, and/or that the bubbles were shelled, the experiments were repeated in the diluted aqueous/xanthan gum gel mixture. As noted above, the diluted gel mixture was sufficiently viscous to enable a UCA to be manually injected into the region of interest. The UCA could then be examined under a microscope to ensure that the agent in the region of interest was an individual microbubble (as opposed to a mass of microbubbles). Due to the viscosity of the solution, each UCA would remain in the region of interest for several minutes, indicating that the bubbles were shelled and stable. As can be seen in FIGS. 5A and 5B, diluted xanthan gum gel did not affect the dynamics adversely, and the fit is remarkably good. The measured peak negative pressure and fitted initial bubble radius, $R_0$, are 340 kPa and 1.5 µm, respectively. As with the previous data, these bubbles also exhibit nearly linear oscillations.

Figure 6A:
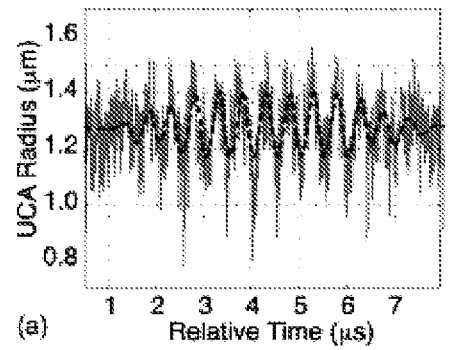
Figure 6B:
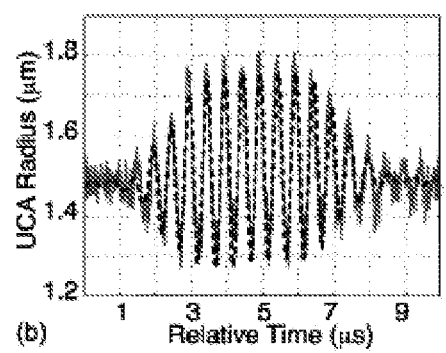
Figure 7A:
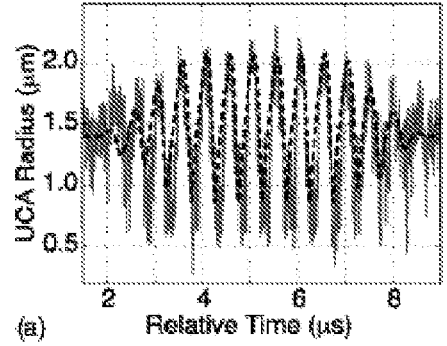
Figure 7B:
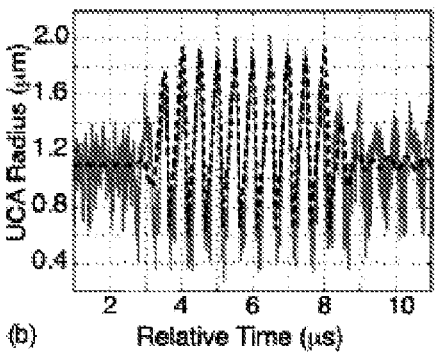

Sample response curves from a single element transducer (i.e., a transducer configured for therapeutic ultrasound rather than for imaging ultrasound) are shown in FIGS. 6A, 6B, 7A, and 7B. These experiments were performed both in water and aqueous xanthan gum gel mixtures. In FIG. 6A, (Optison™), data from a ten-cycle tone burst were averaged over 37 pulses. In FIG. 6B, (Optison™), data from a ten-cycle tone burst were averaged over 40 pulses. In FIG. 7A, (Sonazoid™), data from a ten-cycle tone burst were averaged over 5 pulses. In FIG. 7B, (Sonazoid™), data from a ten-cycle tone burst were averaged over 40 pulses. The measured peak negative pressures and fitted ambient bubble sizes are summarized in Table I (FIG. 8). The relatively poor SNR in FIG. 6A is likely due to the bubble not being in the center of the laser beam. Nonlinear bubble oscillations were especially evident in FIGS. 6B and 7B, presumably due to the increased pressure amplitudes. Although these longer tone bursts are not very relevant to imaging applications (which utilize short diagnostic pulses), variable pulse lengths can be used to explore issues such as shell fatigue and microbubble stability.

The fitted ambient sizes (from Table I in FIG. 8) are consistent with known UCA bubble sizes. Based on FIGS. 5A-7B, it can be concluded that the good fit of the Morgan model to the experimental data, both in water and diluted gel, is evidence that light scattering can be beneficially employed in measuring individual UCA dynamics. Further experiments indicated that these techniques can also be applied to UCA clusters (i.e., masses of microbubbles), not just individual bubbles.

One of the advantages of the light scattering technique discussed above is its ability to make high temporal resolution measurements over long time scales. The following results are based on observations of UCA microbubbles subjected to consecutive pulses from the Ultramark 4Plus™. For slowly evolving microbubbles, the data were combined data for groups of ten pulses, while for quickly evolving microbubbles, the data were examined for each individual pulse.

When fitting the evolution data to the Morgan dynamic model, there is always the question of which of the two unknown parameters ($R_0$ and the product $\epsilon\mu_{sh}$) to change in order to obtain a good fit. Because the shell data that are collected might be compromised (e.g., from dislodging, or crumpling, or due to changes in permeability), varying the shell parameter (product $\epsilon\mu_{sh}$) was preferred.

Slowly Evolving Agents:

To follow the slow evolution of UCAs, the pressure amplitude employed was approximately 130 kPa. This pressure amplitude is lower than the fragmentation thresholds found in the literature for the UCAs utilized. The studies providing the thresholds were looking at relatively fast destruction mechanisms, not slow decay mechanisms. A more relevant comparison is likely to be the slow decay of backscattered signals for UCAs subjected to clinical ultrasound.

FIGS. 9A-9C graphically illustrate the slow evolution of a Sonazoid™ microbubble in water, collected in three successive groups of ten pulses. Significantly, a good fit was obtained without having to change the shell parameter; it was kept constant at 2.0 nm Pa s. However, $R_0$ was increased between groups (from 1.2 to 1.9 µm; see Table II in FIG. 10). That is, the Sonazoid™ microbubble appears to be growing with successive pulses. This slow growth phenomenon was not observed with Optison™ bubbles. Two physical interpretations can be made. First, the lipid shell may have been partially compromised before the experiment began. Although possible, this trend has been observed from many different datasets. Second, during expansion or compression, the lipid shell may alternatively become semi-permeable. If it is assumed that the bubble is filled initially with perfluorobutane (PFB) and the water contains air; then because of the higher diffusivity of air, diffusion of air into the bubble will occur at a faster rate than diffusion of PFB out of the bubble.

Thus, at least initially, the bubble can grow. Again, it is emphasized that FIGS. 9A-9C show successive segments in one sequence of data. At about 1 ms between segments (equal to the burst PRF), the total elapsed time is about 30 ms.

A summary of the parameters for FIGS. 9A-9C is provided in Table II (FIG. 10). Previously reported data indicates that Sonazoid™ microbubbles dissolve after each pulse; however, such data were generated using about twice the pressure amplitude. It is likely that at those higher pressures, gas may be forced through the shell during compression.

Quickly Evolving Agents:

For this study, the pressure amplitude was increased to 340 kPa for Optison™ and 390 kPa for Sonazoid™. Previous studies report that the decay rate of the backscattered signal for Optison™ increased at these higher pressures, and that Sonazoid™ also showed a decay, although at a slower rate. Other studies indicate that these pressures are above the fragmentation threshold.

FIGS. 11A-11D graphically illustrate Optison™ response curves (i.e., RT curves) for individual (i.e., non-averaged) pressure pulses from the Ultramark 4Plus™ in the diluted aqueous/xanthan gum solution/gel. In FIGS. 11A-11C, the microbubble response comes from consecutive pulses. A single pulse is skipped, and then the data illustrated in FIG. 11D were collected. In terms of pulses, the Figures illustrate the dynamical response from pulses 1, 2, 3, and 5.

There appears to be a second series of oscillations developing in FIGS. 11B-11D. These signals may be due to the arrival of a second microbubble. Referring to the first major peak, in FIG. 11A the Morgan model corresponds to the data rather well. The fit is for a 1.5 μm radius bubble, with a shell parameter of 6.0 nm Pa s. In FIG. 11B, the fit is still acceptable; however, there are large amplitude "spikes" in the dataset. Such spikes were often observed immediately before, or during microbubble destruction, and may be related to a crumpling of the shell (shell crumpling has been previously observed). In FIGS. 11C and 11D, the model must be adjusted by decreasing the shell parameter (keeping the radius fixed). That is, the shell of the microbubble from which the scattered light was collected appears to be compromised. The parameters for this dataset are summarized in Table III (FIG. 12).

FIGS. 13A-13F graphically illustrate RT curves for optical scattering data collected from a Sonazoid™ bubble in water, while the bubble was undergoing an evolution during consecutive pulses (one pulse is not shown between the last two pulses, i.e., a pulse was skipped between the RT curves of FIGS. 13E and 13F). Referring to FIGS. 13A-13D, the shell parameter is fixed, but the ambient bubble radius was increased from 0.8 μm to 1.2 μm to maintain a good fit (i.e., to achieve the fit indicated by the dashed line). The Sonazoid™ bubble appears to absorb air from its surroundings before the shell is broken. By pulse number 5 (i.e., FIG. 13E), the shell is compromised. Also note the apparent non-linearity of the bubble motion. The parameters for this data set are summarized in Table IV (FIG. 14). To summarize the data discussed above, at these modest pressures, Sonazoid™ microbubbles appear to have a semi-permeable shell when insonified, allowing air to be absorbed, and causing the bubble to grow. Both Optison™ and Sonazoid™ UCAs appear to show damage to the shell after two or more pulses. It should be noted that these results are examples involving individual microbubbles. It would be necessary to examine many such cases before a conclusion could be drawn as to the "average" response of a particular microbubble.

Spectral Analysis:

Light scattering data may also be suited to fast analysis by examining the spectrum of the signals. Toward this eventual goal, the power spectral densities (PSD) of the R(t) curves discussed above were examined. FIG. 15 graphically illustrates normalized PSDs. There are significant fundamental peaks in the PSDs of FIG. 15, related to the (real) resonance frequency of the system. Furthermore, apparent sub-harmonic and harmonic components were often observed. A more thorough analysis of these signals may eventually lead to better information about the response curves, or R(t) that could be used to optimize the agents for imaging and therapy.

The above empirical studies evaluated the feasibility of using light scattering to measure the radial pulsations of individual ultrasound contrast microbubbles (Optison™ or Sonazoid™) subjected to pulsed ultrasound. Experiments performed in a highly diluted xanthan gum mixture were used to verify that individual encapsulated microbubbles could be investigated. The evolution of individual contrast microbubbles was observed over several consecutive acoustic pulses, suggesting that shell permeability and/or shell fatigue are important consequences in the evolution of microbubbles. It appears that light scattering can be used to better understand the physical interaction between ultrasound pulses and contrast agents, and eventually be used to evaluate shell parameters and explore shell fatigue, leading to better agent design.

Summary of Initial Study of Optison™ and Sonazoid™ Bubbles:

Scattered light was collected from single UCA bubbles while the individual bubbles were oscillated with a diagnostic ultrasound machine. The empirical data were fitted with the Morgan model with good success. It was assumed that the thickness of the shell was relatively constant for a range of bubble sizes. Based on the trial fitting of the empirical data, it was determined that the shell parameters $\epsilon_l ush=6$ nm Pa s for Optison™ and $\epsilon_l ush=2$ nm Pa s for Sonazoid™ are acceptable. Those parameters were then input in the Morgan model so that the model was fitted to the empirical data with the initial value being the only variable. The empirical data were filtered using a 10 MHz low-pass filter. It was observed that the Morgan model correctly described the UCA bubble's response to longer acoustic tone bursts (i.e., therapeutic ultrasound) as well the bubble's response to short pulses from a diagnostic ultrasound instrument. The empirical data collected while oscillating UCAs to destruction indicate that it usually takes some time or several cycles for ultrasound pulses to disrupt the UCA bubbles. The destruction process appears to include distortion of bubble shape, the generation of partial defects or ruptures of the UCA shell, and an increase in the magnitude of this distortion, with the expansion of the UCA shell followed by the complete rupture of the UCA shell, yielding a free gas bubble. It is likely that shell fragments may still affect the nearby acoustic field and scattering field. It was observed that the damping characteristic of a UCA shell contributes to the resonance frequency shift to a lower frequency. When a UCA bubble is broken, the resonance frequency of the bubble is observed to increase (based on spectral analysis of the data).

Different Shelled UCA Models:

As noted above, many different dynamic models have been developed to describe the motion of microbubbles or spheres. A significant aspect of the light scattering technique disclosed herein is that the collected data (i.e., the RT curves) can be fitted to many different models. The number of variables being fitted can be minimized by acquiring data corresponding to as many of the model variables as possible. As discussed above, ambient pressure can be measured using a hydrophone while the scattered light is collected, eliminating pressure as a variable. The initial radius of a microbubble can be measured optically (i.e., using a microscope and a camera), or literature-based values can be used for the initial radius, eliminating yet another variable. Preferably, the only unknown variables involved in the fitting process relate to shell parameters, which to date, have been difficult to empirically measure. The following discussion is related to additional models.

The de Jong's model, Church's model, Hoff's model, and Sarkar's model are each based on the general RPNNP equation (i.e., Eq. (1)), which as noted above, describes the response of a spherical bubble to a time-varying pressure field in an incompressible liquid.

The assumptions for the RPNNP equation are: (1) the motion of the bubble is symmetric; (2) the wavelength of ultrasound is much larger than the bubble radius; (3) no rectified diffusion occurs; and, (4) the bubble contains gas or vapor, which is compressed and behaves according to the gas law, with the polytropic parameter held constant.

de Jong's Model:

De Jong modified the RPNNP equation to account for shell friction ($\delta_f$, included in $\delta_{tot}$) and elasticity ($S_p$) parameters as follows:

$$\rho_L R \ddot{R} + \frac{3}{2} \rho_L \dot{R}^2 = \qquad (4)$$
$$P_g \left(\frac{R_0}{R}\right)^{3\kappa_1} + P_v - P_0 - \frac{2\sigma}{R} - 2S_p\left(\frac{1}{R_0} - \frac{1}{R}\right) - \delta_{tot} \omega \rho_L R \dot{R} - P_a \cos(\omega t)$$

where $S_p = 6 G_s d_{se}(R/R_0)^3$, and $G_s$ is the shell shear modulus, and $d_{se}$ is the shell thickness. The total damping parameter is given by:

$$\delta_{tot} = \delta_{th} + \delta_R + \delta_\eta + \delta_f \qquad (5)$$

and thermal damping constant is given by:

$$\delta_{th} = \frac{1}{\omega_0 \omega} \frac{p_0}{\rho_L a^2} \text{Im}\left(\frac{1}{\Phi}\right) \qquad (6)$$

The formula of $\Phi$ is adapted from Devin. The radiation resistance damping constant is given by:

$$\delta_R = \frac{\omega^2 a}{\omega_0 c} \qquad (7)$$

and the viscosity damping constant is given by:

$$\delta_\eta = \frac{4\eta_L}{\omega_0 \rho_L R^2} \qquad (8)$$

where $\eta_L$ is the liquid shear viscosity. The shell friction parameter is:

$$\delta_f = \frac{12 \eta_s d_{se}}{\omega_0 \rho_L R^3} \qquad (9)$$

where $\eta_s$ is the shell shear viscosity. The polytrophic exponent is:

$$\kappa_1 = \text{Re}\left[\frac{1}{\Phi(R,\omega)}\right] \qquad (10)$$

Church's Model:

In Church's work, a Rayleigh-Plesset-like equation describing the dynamics of shelled gas bubbles was derived. It was assumed that a continuous layer of incompressible, solid elastic shell with damping separates the gas bubble from the bulk Newtonian liquid. The elastic surface layer stabilizes the bubble against dissolution by supporting a strain that counters the Laplace pressure. Viscous damping is considered in this model, which is as follows:

$$\rho_s R_1 \ddot{R}_1 \left[1 + \left(\frac{\rho_L - \rho_s}{\rho_s}\right)\frac{R_1}{R_2}\right] + \rho_s \dot{R}_1^2 \left\{\frac{3}{2} + \left(\frac{\rho_L - \rho_s}{\rho_s}\right)\left[\frac{4R_2^3 - R_1^3}{2R_2^3}\right]\frac{R_1}{R_2}\right\} = \qquad (11)$$
$$P_{G,eq}\left(\frac{R_{01}}{R_1}\right)^{3\gamma} - P_\infty(t) - \frac{2\sigma_1}{R_1} - \frac{2\sigma_2}{R_2} -$$
$$4\frac{\dot{R}_1}{R_1}\left[\frac{V_s \eta_s + R_1^3 \eta_L}{R_2^3}\right] - 4\frac{V_s G_s}{R_2^3}\left(1 - \frac{R_{e1}}{R_1}\right)$$

where $\rho_s$ is the shell density, $\sigma_1$ is the surface tension of the gas-shell interface, $\sigma_2$ is the surface tension of the shell-liquid interface, $P_{G,eq} = P_0$ for the surface layer permeable to gas, and:

$$P_\infty(t) = P_0 - P_a \sin(\omega t) \qquad (12)$$
$$V_s = R_{02}^3 - R_{01}^3$$

$$R_{e1} = R_{01}\left[1 + \frac{\left(\frac{2\sigma_1}{R_{01}} - \frac{2\sigma_2}{R_{02}}\right)\frac{R_{02}^3}{V_s}}{4G_s}\right] \qquad (14)$$

Hoff's Model:

A simplified equation was derived from Church's equation by Hoff, for the case of thin shell, $d_{se}(t) \ll R_2$:

$$\rho_L R \ddot{R} + \frac{3}{2}\rho_L \dot{R}^2 = P_0\left[\left(\frac{R_0}{R}\right)^{3\gamma} - 1\right] - \qquad (15)$$
$$4\eta_L \frac{\dot{R}}{R} - 12\eta_s \frac{d_{se} R_0^2}{R^3} \frac{\dot{R}}{R} - 12 G_s \frac{d_{se} R_0^2}{R^3}\left(1 - \frac{R_0}{R}\right) - P_i(t)$$

Sarkar's Model:

Chatterjee and Sarkar developed a new model for encapsulated contrast agent microbubbles, as follows:

$$\rho_L \left( R\ddot{R} + \frac{3}{2}\dot{R}^2 \right) = \qquad (16)$$

$$\left( P_0 + 2\frac{\sigma_i}{R_0} \right)\left( \frac{R_0}{R} \right)^{3\gamma} - 4\eta_L \frac{\dot{R}}{R} - 2\frac{\sigma_i}{R} - 4\frac{\kappa^s \dot{R}}{R^2} - [P_0 + P_{drive}(t)]$$

This model assumes the encapsulation of a contrast agent to be an interface of infinitesimal thickness with complex interface Theological properties. The interfacial tension, $\sigma_i$, and dilatational viscosity $\kappa^s$ are unknown interface and shell parameters.

Figure 16:
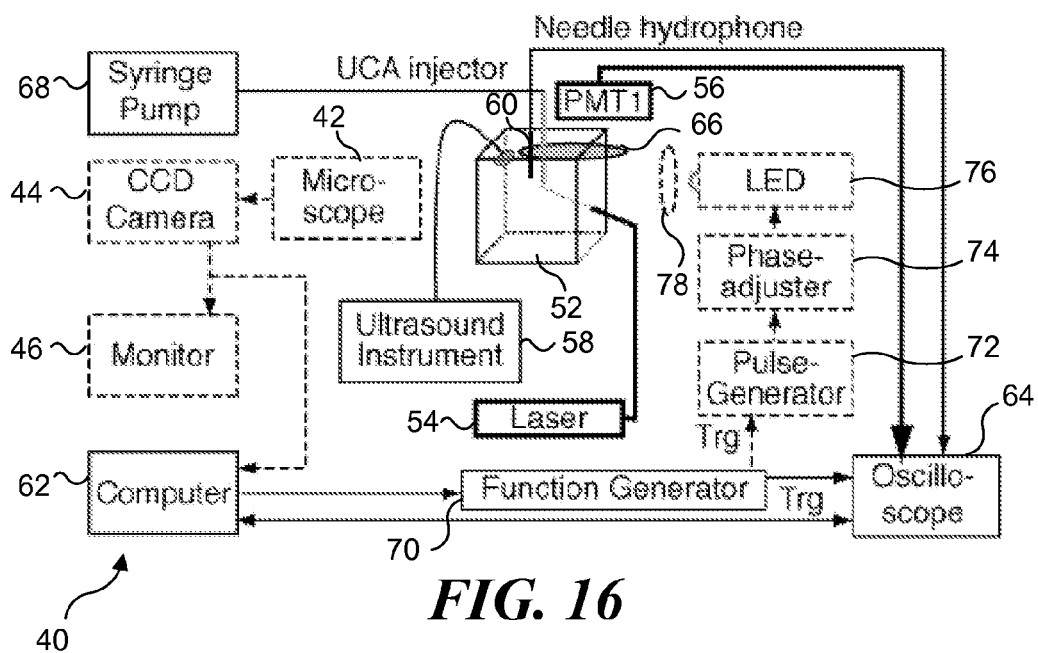

Additional light scattering empirical studies were performed measure the dynamic response of individual Sonovue™ bubbles to the driving acoustic pulse using a system 40 schematically illustrated in FIG. 16. Note that the system of FIG. 16 is based on the system of FIG. 2, and includes an optional microscope 42, an optional CCD camera 44, and an optional monitor 46 to enable the radius of the microbubble to be empirically measured, generally as discussed above. In brief, the highly diluted Sonovue™ suspensions were injected into the region of interest (ROI defined herein as being a small volume 52 where the ultrasound and laser beams intersected with Sonovue™ bubbles) using a syringe pump 68 (e.g., a 74900™ series, Cole-Parmer Instrument Co., Vernon Hills, Ill., USA) at a rate of 10 ml/h with a tube (0.5 mm inner-diameter). The driving acoustic pulses were sent from a probe of a diagnostic ultrasound instrument 58 (e.g., an Ultramark 4Plus™, ATL-Philips, USA) operated in M-Mode at 1-kHz pulse-repetition-frequency (PRF) and monitored using a calibrated needle hydrophone 60 (e.g., from NTR Systems Inc., Seattle, Wash., USA). An HeNe laser 54 (Melles Griot, Carlsbad, Calif., USA) was used as a light source. The waist of the laser beam was focused to less than 100 μm at the ROI by a lens (not shown). The scattered light signals from the microbubbles in the ROI were collected and focused by another lens 66 onto a photo-multiplier tube (PMT) detector 56 (e.g., a Hamamatsu, Model 2027™). The output signals from the PMT and the hydrophone were recorded using a high-speed digital oscilloscope 64 (e.g., from LeCroy, Chestnut Ridge, N.Y., USA) in sequence mode provided by a function generator 70, and then transferred to a computer 62 waiting from post-processing using a MatLab program (Mathworks Inc., Natick, Wash., USA). Optionally, a pulse generator 72 can be triggered by the function generator to produce a pulse signal applied to a phase adjuster 74, to produce light pulses with an LED 76 that are focused by a lens 78 into volume 52.

Figure 17A:
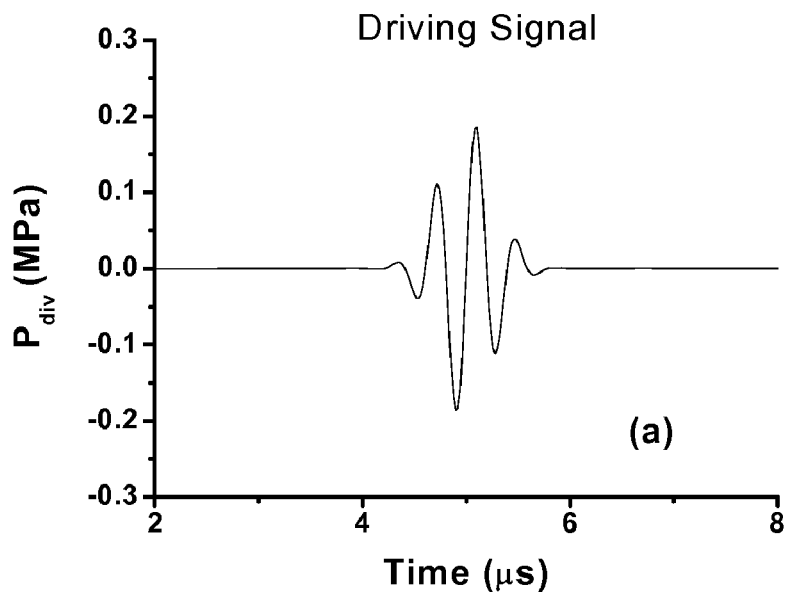
FIG. 17A illustrates a modified Gaussian pulse used to simulate a driving signal for different dynamic models.
Figure 17B:
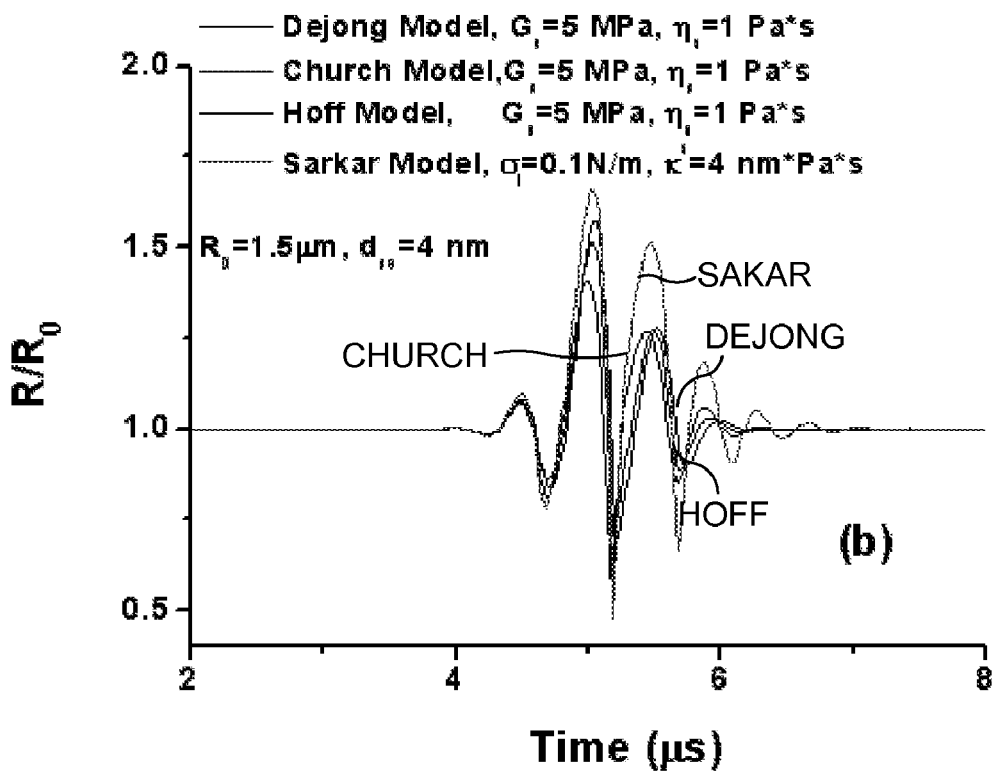
FIG. 17B illustrates typical bubble responses using four different dynamic bubble models.

Results and Discussion:

The four models (i.e., de Jong's model, Church's model, Hoff's model and Sarkar's model) noted above in the previous section were "run" with the same modified Gaussian pulse, $$P_{div} = P_0 \sin[2\pi f(t-t_c)] \exp[-\pi^2 h^2 f^2 (t-t_c)^2] \qquad (17)$$

with $t_c$=5 μs and h=⅓. The results indicate that each model appears to provide substantially similar results in a certain parameter range. FIGS. 17A and 17B graphically illustrate the response of a 1.5 μm radius bubble subject to a 2.5 MHz modified Gaussian pulse with a peak negative pressure of 0.2 MPa. FIG. 17A illustrates the modified Gaussian pulse is used to simulate the driving signal, while FIG. 17B illustrates typical bubble responses using the four above noted dynamic bubble models. The parameters used for the simulation are given below.

$\rho_L$=10³ kg/m, density of a Newtonian liquid
$P_0$=101300 Pa, ambient pressure
$P_v$=2330 Pa, vapor pressure (Chang et al, 1999)
$\sigma$=0.07275 N/m, surface tension
$\rho_g$=1.161 kg/m³, gas density
$C_p$=240.67, heat capacity at constant
$K_g$=0.00626, thermal conductivity (for air at 300K and 1 atm)
c=1500 m/s, acoustic velocity
γ=1, gas adiabatic constant
$\eta_L$=0.001 Pa×s, liquid shear viscosity (Church et al, 1994)
$\rho_s$=1100 Kg/m³, shell density (Church et al, 1994)
$\sigma_1$=0.04 N/m, surface tension of the gas-shell interface (Church et al, 1994)
$\sigma_2$=0.005 N/m, surface tension of the shell-liquid interface (Ibid.)

As noted above, and as illustrated in FIG. 17B, each model appears to provide substantially similar results within a certain parameter range. However, if the selected shell parameters (e.g., shell viscosity q, and shell shear modulus Gs), are out of a certain range, these models will likely produce different responses. Since the same shell parameters are used in the de Jong, Church, and Hoff models, the studies here are focused on these three models. FIGS. 18A-18C graphically illustrate results provided by these three models with varying parameters. Each of the three models provides substantially the same result with appropriately selected parameters (FIG. 18A), whereas the simulation results become different from each other with increasing Gs (e.g., Gs>50 Mpa; FIG. 18C) or decreasing $\eta_s$ (e.g., $\eta_s$<0.1 Pa*s; FIG. 18B). Additional non-linear behaviors can be observed with the changed shell parameters, which suggests that each of the three models might have similar linear responses, while their non-linear responses differ. Therefore, although the acoustic driving parameters are controllable, it is still difficult to tell which model is 'better' without knowing the shell parameters a priori. Further studies on UCA shell parameters are important and necessary to make it possible to rank the various models.

Figure 19B:
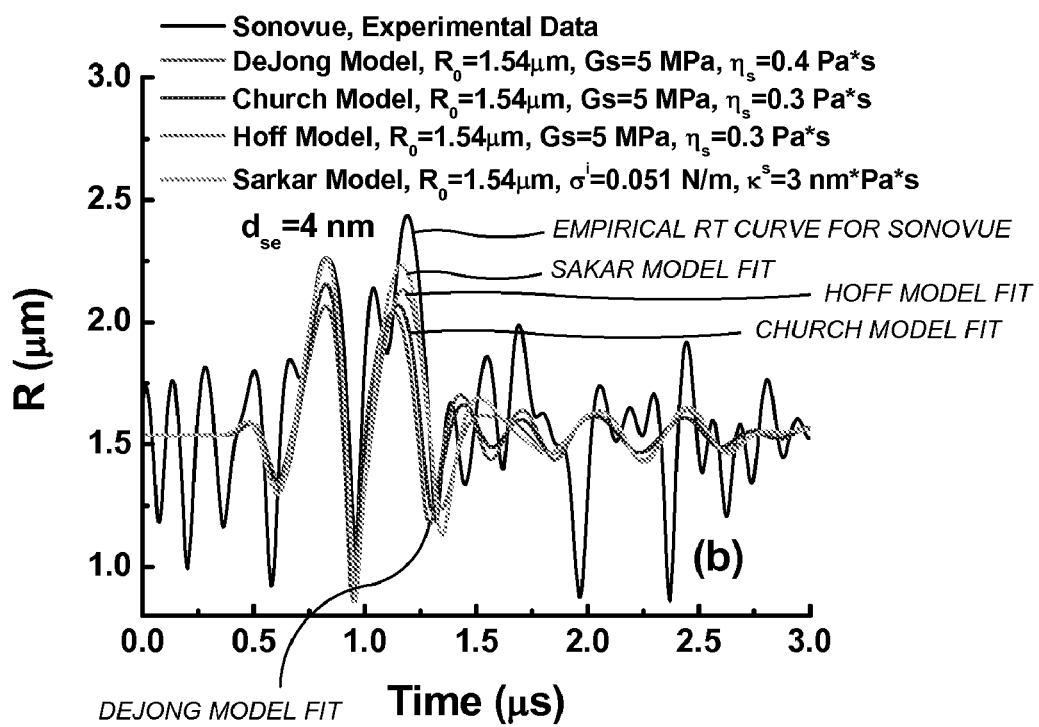

Although as noted above different models can give similar simulations results with appropriately selected parameters, to verify the accuracy of the these models (i.e., de Jong's model, Church's model, Hoff's model, and Sarkar's model) the experimentally measured Sonovue™ bubble RT curve can be fitted to each of the four models with selected fitting parameters. Literature reports that Sonovue™ bubbles have a very thin lipid shell whose thickness is assumed to be 4 nm. Three unknown fitting parameters were chosen for present work: $R_0$, Gs, and $\eta_s$ in de Jong, Church, and Hoff's models, and $R_0$, $\sigma_i$, and $\kappa^s$ in Sarkar's model. Minimum standard deviation evaluation is applied to determine the best fitting. FIGS. 19A and 19B graphically illustrate a comparison between the experimental data and simulated results, with the Sonovue™ bubble oscillating with a driving pressure amplitude of about 0.15 MPa. The results indicate that Sonovue™ bubbles behave in a strongly non-linear motion. The likely explanation for this observation is that the lipid shells of Sonovue™ bubbles are very thin and relatively permeable. Therefore, the properties of the Sonovue™ bubble shell likely change when the bubble is driven by acoustic pulses, which induces the observed non-linear behavior.

FIG. 19B graphically illustrates that the empirically measured scatter light RT curve for a Sonovue™ bubble can be fitted reasonably well to each of the four models. The fitted initial radius for each model converts to 1.54 μm, which agrees with the manufacturer's data. However, at the later stages of the driving pulse, the fitting results can not follow the measured non-linear response, which suggests that a better model is needed in order to satisfactorily account for the non-linear response of a Sonovue™ bubble. The Sonovue™ bubble's non-linear behavior might result from the change of bubble shell parameters during its oscillation. If it is assumed that the fitting results for experimental data are acceptable, the relationship between Sonovue™ shell parameters, e.g., shear modulus Gs and shear viscosity $\eta_s$, and bubble initial radius ($R_0$), can be obtained by fitting the pooled experimental data with the selected numerical model. Since all four of these models yield similar simulation results for the experimental data (as shown in FIG. 18B), it is reasonable to select any one of the four models to quantify the bubble shell parameters. In this study, Hoff's model was ultimately selected, since it is based on a thin-shell assumption. In order to simplify the computational process, the lipid shell thickness for the Sonovue™ bubble was assumed to be a constant value of 4 nm, as reported in the literature.

FIGS. 20A and 20B graphically illustrate that both shell shear modulus and shear viscosity increase with increasing initial radius, which implies the shell properties of UCA bubbles are not homogeneous, and may be related the bubble size. FIG. 20A graphically illustrates the change of the shell shear modulus as a function of radius, while FIG. 20B graphically illustrates the change of the shell viscosity as a function of radius. These results suggest that UCA shell properties will significantly affect bubble dynamic behaviors. However, considering the lack of effective methods to measure the shell properties directly, further efforts on the study of UCA shell parameters using the light scattering techniques disclosed herein are imperative for improving UCA development and applications.

Measuring Multiple UCA Bubble Dynamics Using Light Scattering:

The single Optison™ and Sonazoid™ studies discussed above prove the value of light scattering in studying the dynamics of single bubbles. Additional empirical studies were performed to study a group of UCA bubbles using scattered light. Such group dynamics are important, as in clinical conditions, masses of UCAs (as opposed to individual bubbles) are employed. Such research has indicated that at a relatively low driving power, UCA bubbles are observed responding to the acoustic driving wave and oscillate. At relatively higher driving powers, the destruction of UCA bubbles is observed (as expected). Significantly, the harmonic response of UCA bubbles can be observed at varied driving powers.

When studying multiple UCA bubbles, the analysis is more complex, concerning both optics and acoustics. Statistically speaking, the properties of UCA bubbles can be estimated by its distribution profile, provided by the manufacturers. The profiles can be described with a known statistics algorithm, such as Gaussian distribution, to make it simpler to model distribution of UCA bubbles, and therefore analyze the statistical characteristics of UCA bubbles. Once the statistics package is determined, the properties, such as mean and variation, can be applied to the model to perform simulation. UCA bubbles are so small that there are about half a billion of them in a single milliliter. For Optison™, there are $5 \times 10^8$-$8 \times 10^8$ individual bubbles per milliliter. Since so many bubbles are involved, it is difficult to know the number of bubbles in the region of interest.

From an acoustical standpoint, the measured acoustic pressure may not correctly describe the actual acoustic field that activates the UCA bubbles, since the UCA cloud alters the acoustic driving field. Further, the driving pressure is attenuated inside the UCA cloud. This obvious impact is indeed observed in the measurement of acoustic pressure in the field. However, the acoustic measurement is necessary to monitor the pressure level outside the targeted UCA cloud. The pressure signals also trigger data collecting events, which means that the pressure measurement cannot be used to describe the pressure on each individual UCA bubble for modeling and data fitting, as it was in the single UCA studies described above.

From an optical standpoint, the laser beam is affected similarly, in that a mass of bubbles scatters light differently than an individual bubble. As a whole, the UCA bubbles in the path of the laser beam are not homogeneously distributed. The laser beam itself is not homogeneous either, having a transverse intensity distribution. This does not impact individual UCA bubbles; however, the inhomogeneous cross-distribution of the laser beam means that a UCA bubble at the center of the laser beam encounters more light than a UCA bubble near the edge of the laser beam.

To address these issues, the RT curves discussed above are modified, to achieve an effective RT curve. The effective RT curves are computed from the light scattering data, based on the assumption that each UCA bubble is separated far enough from its neighboring bubbles such that there is no attenuation to the incident light intensity on each UCA bubble. It is also assumed that the laser beam is homogeneous, which means each UCA bubble scatters laser light as if there is only one UCA bubble in the region. The effective scattered light intensity of the collected data combines the contributions from every bubble.

The multiple bubble study employed an HDI 5000™ ultrasound system, which is able to operate in many modalities, including B-Mode, M-Mode and Pulse-Doppler Mode, each of which was used in the multiple bubble study. The HDI 5000™ system (probe) functions as an acoustic source; and, each modality features a different pulse length and central frequency. Every modality can provide either low or high power. The intact UCA bubbles' response to acoustic driving pulses, and the destruction of the UCA bubbles, are of great interest in revealing the UCA bubbles' properties. Since today's diagnostic ultrasound systems perform harmonic imaging with UCA bubbles mainly in a B-Mode at extremely low power, much of the data collected in the multiple bubble study were obtained using the B-Mode at a low driving power (MI).

FIG. 21A graphically illustrates a typical effective RT curve of a mass of UCA bubbles (i.e., the effective RT curve of UCA bubbles in B-Mode at MI=0.04), and FIG. 21B graphically illustrates the power spectrum of the UCA bubbles' response. These Figures provide an understanding of how the light scattering data were processed. The data utilized in these Figures were collected in the B-Mode with MI=0.04, where the fundamental frequency in B-Mode is about 2 MHz. The effective RT curve was generated from a light scattering signal that monitors the dynamic oscillation of the UCA bubbles. In FIG. 21B, the power spectrum of the UCA bubbles' dynamics is lower than 2 MHz. This shift of fundamental frequency between the bubbles' response and that of the driving pressure is discussed below. The main focus of the multiple bubble study was on the spectrum properties of UCA bubbles' response. However, the destruction properties of UCA bubbles are of interest as well. In the following discussion, where the focus is on spectral analysis, the RT curves may not be provided.

It is recognized that the UCA cloud will scatter some of the incident acoustic beam, which will result in the attenuation of the acoustic pressure on the UCA bubbles in the path of acoustic beam. Thus, the UCA bubbles are not homogeneously driven, which further complicates the analysis of the collected data. Because the region of interest upon which the PMT is focused is very small, it is assumed that all the UCA bubbles are homogeneously activated. Note that as indicated in FIG. 21A, the effective expansion of the UCA bubbles is relatively small (i.e., the expansion is only about 5% of their ambient sizes).

The B-Mode:

In the B-Mode, the driving power (MI) starts as low as 0.03 (the lowest HDI 5000™ power setting). FIG. 21C graphically illustrates two examples (i.e., one a solid line, and one a dashed line) of the power spectrum at MI=0.03. The harmonic response of each example is slightly different, possibly due to the difference of the specific local UCA bubbles. Significantly, as indicated by each example, the UCA bubbles respond to the acoustic source, even though the driving pulses are very weak. Further, the power spectrum reveals strong fundamental components, while a harmonic component is observed as well. The harmonic component can be particularly significant, as the solid line indicates. When compared with the driving pulse central frequency (2 MHz—not shown), it is evident that the fundamental frequency of the UCA bubbles' response is shifted relative to the frequency of the driving pressure, as will be noted in FIG. 21B. It is also noted that the response of the second group of UCA bubbles (i.e., the second example, whose data are shown in the graph with a dash line) indicates different spectral characteristics in the power spectrum. That is, the feature of the fundamental component in the power spectrum of the UCA bubbles' response is different.

FIG. 22 is a composite graph illustrating the power spectrum of UCA bubbles driven by different acoustic power (MI) settings, using the B-Mode. As indicated in the Figure, the fundamental frequency shifts to a lower frequency when the driving power is lower than MI=0.05, clearly, responding differently to different acoustical driving powers. Because higher acoustic power settings can destroy UCA bubbles, lower power settings are generally preferred (unless UCA destruction is desirable, as in the case of using microbubbles to deliver therapeutic agents encapsulated in the bubbles). It should be noted that the data graphically illustrated in FIG. 22 were generated from intact UCA bubbles oscillating due to acoustic pulses. FIG. 22 shows the power spectrum of UCA bubbles' response with a driving power at MI=0.03, 0.03+, 0.04, 0.04+, 0.05, 0.05+, 0.06 0.07, and 0.11, respectively. The + sign refers to the middle level of MI for the HDI 5000™ system, between two consecutive defined MI settings. The selection of MI is based on the smallest step of power increase starting from the lowest available value, but the step is greater between the last two highest powers.

Referring to FIG. 22, it should be noted that the fundamental frequency of the bubbles' response varies. When the driving power is lower than MI=0.05, the fundamental component (at about 2 MHz) of the bubbles' response shifts to a lower frequency. When the driving power is 109 (equal to or greater than MI=0.05), the fundamental frequency seems to match satisfactorily (though not perfectly) the acoustic driving frequency. Further, the harmonic frequency components vary based on driving power, which can be observed in both low and high power drive settings. There seems no great advantage to use higher driving power settings to generate harmonic components. A second harmonic frequency shift (at about 4 MHz) basically follows the trend of the fundamental frequency. When the fundamental frequency shifts toward a lower frequency, the corresponding second harmonic frequency also shifts toward a lower frequency. Finally, the sub-harmonic component (at about 1 MHz) can be identified in most of the examples, but the power of sub-harmonic component is very weak. In most of the examples, the harmonic components at 3 MHz, 5 MHz and 7 MHz can be identified, especially for examples employing a higher driving power. Overall, the various examples illustrated in FIG. 22 do not suggest that the generation of harmonic components in the response of the bubbles to an acoustic driving is highly dependent on the power of operation employed during the insonification, while the bubbles are intact.

Further statistical analysis of the data to determine why the fundamental frequency, as well as harmonic frequencies, of the response of the bubbles shifts when a low driving power is employed did not indicate any dependence of fundamental frequency of the bubbles' response to the driving powers. A higher driving power increases the chance of generating more (and stronger) harmonic components, as well as sub-harmonic components, even though the power of sub-harmonic components are usually much smaller than that of harmonic components. The statistical analysis confirmed that both the shift of harmonic frequencies (second harmonic and third harmonic frequencies) and the shift in the fundamental frequency are in the same direction (i.e., a shift to lower frequencies), although the shifts in the harmonic frequencies are greater in magnitude.

It appears that there is a pressure threshold (MI=0.05 in the examples of FIG. 22) in the B-Mode, which impacts the UCA bubbles' response. Because the frequency shift of UCA bubbles' response does not relate to the driving power, when the driving power is low, the cause of the frequency shift must come from the UCA bubbles themselves. The frequency shift (to a lower frequency at a low driving power) is likely due to a size distribution of the UCA bubbles, since the majority of the UCA bubbles are in the range between 1 μm and 2 μm in radius. When the driving pressure is small, the UCA bubbles may oscillate with the driving wave, as well as experience self-resonance. The coupling of the oscillations could result in the change of spectral features. When the driving pressure is sufficient, the forced oscillation overcomes the self-oscillation, to emerge as a main contributor to the spectra, resulting in the fundamental frequency resembling that of the driving power.

Regardless of the spectral features, it is noteworthy that at an MI as low as 0.03, the harmonic components in the responses of UCA bubbles can still be generated. This finding indicates that the harmonic component in the response of UCA bubbles can be generated as long as the bubbles are forced to oscillate. However, it is recognized that UCA bubbles will not oscillate strongly when the driving power is low, and the signal level indeed could be extremely low. Thus, when the driving power is low, the harmonic components may not be distinguishable from noise.

FIGS. 23A and 23B are composites. The development of UCA bubbles during consecutive insonification in one data sequence (collection) is graphically illustrated as RT curves in FIG. 23A, and as power spectrums in FIG. 23B. Each sub-figure in the composite represents an averaged result over the duration of a consecutive activation.

When multiple UCA bubbles are involved, if they are in close proximity, they are likely interact with one another to some degree. The data collected to generate FIGS. 23A and 23B were collected with an MI of 0.05+. In the RT curves of FIG. 23A, the effective radius of the UCA bubbles continues to increase during insonification. The magnitude of the forced oscillation builds up initially and then slows. It appears that none of the UCA bubbles were burst during the activation, because there is no significant sudden increase of effective radius that would indicate breaching of the shell. In the corresponding power spectrums of FIG. 23B, the fundamental frequency of responses of the UCA bubbles does not change, which suggests that there is no significant physical change to the bubbles in this area. Under this condition, the gain of ambient effective radius of the UCA bubbles in the area suggests that the increase in light scattering is primarily due to an adjustment of the spatial distribution of bubbles in the area. If the bubbles are closely packed, their expansion is limited by the proximity of neighboring bubbles. As the UCA bubbles oscillate with the acoustic wave, they also interact with one another as well, and thereby alter the spatial distribution characteristics.

It can be noted from FIG. 23A that the effective radius of the bubbles, after an acoustic pulse, is larger than before the acoustic pulse, although the difference is not particularly significant in these examples. FIG. 24 graphically illustrates data averaged over 100 consecutive pulses. The ambient effective radius before the acoustic pulses is about 9 µm, and the ambient effective radius after the acoustic pulses is about 9.5 µm. The data provide no indication that any bubbles are being ruptured, which suggests that the acoustic driving power contributes to the increase of the UCA bubbles' scattering capability. That there is no bubble destruction, or physical change in the bubbles, suggests that the change of the spatial distribution of the bubbles is the key factor in the observed increase in the light scattering capability of the UCA bubbles in the area.

It was also observed that the magnitude of the response of the UCA bubbles falls gradually after segment 220 in FIG. 23A, while these bubbles' ambient scattering capability is still increasing. It is believed that the bubbles' scattering capability is increasing with respect to both light and sound. When the UCA bubbles spread out, they can oscillate more freely, with less interaction, so that both ambient scattering capability and the magnitude of oscillation increase. Meanwhile, the bubbles that encounter the acoustic wave first are able to scatter more energy, and bubbles that encounter the acoustic wave later are driven by weaker acoustic pulses, which results in the decreasing magnitude of oscillation. However, the ambient scattering capability is not affected. This combined effect results in the phenomenon in the RT curves of FIG. 23A that ambient scattering capability keeps increasing, while the amplitude of oscillation first increases and then falls.

The data set graphically illustrated in FIGS. 23A and 23B shows the development of UCA bubbles during insonification at extremely low driving power. It should be noted that UCA bubbles can break even at very low acoustic power levels. As is known, when gas bubbles are released (by the breaking of a shell) and are driven by acoustic pulse, such gas bubbles can suddenly grow in size tremendously. The data set graphically illustrated in FIGS. 25A and 25B relates to such a condition, where UCA bubbles start to break and dissolve during insonification at low MI (=0.05). FIG. 25A includes RT curves of the same group of UCA bubbles during the consecutive insonification, while FIG. 25B shows the corresponding power spectrums. Four consecutive segments (UCA bubbles' response to acoustic pulses) are shown in the Figures. In segments 260 and 262, the RT curves actually reveal a change in the dynamics of the UCA bubbles, when compared with the RT curve of FIG. 20A. The breaking of the UCA bubbles is clearly illustrated with the sudden increase of effective radius in segments 261 and 263. The breakage can also be visualized in the power spectrums of FIG. 25B. The fundamental, harmonic, and sub-harmonic frequencies are clearly seen in segments 260 and 262. The broad increases of the power spectrum in segments 261 and 263 are symbolic of the sudden increases of the effective radius and the breakups of UCA bubbles. Even though the whole sequence is not shown here, the sequence data indicates that additional bubbles are breaking during the insonification. This data set also shows that UCA bubbles may break in groups or individually at a low driving power, depending on the actual input power. The fact that UCA bubbles break gradually at a low MI is also proven in this example. Note that the ambient effective radius does not change from segments 260 to segment 263, which suggests that the number of UCA bubbles broken in segments 261 and 263 is not significant.

It has been shown that the harmonic frequency is generated by UCA bubbles responding to acoustical pressure. If the second harmonic component is sufficiently strong, the RT curve should reflect this phenomenon, which is shown in FIGS. 26A and 26B, with FIG. 26A corresponding to the RT curves, and FIG. 26B corresponding to the power spectrum. The driving power for this data set was MI=0.06. In the RT curve, the waveform of the second harmonic component can clearly be observed, coupled with the fundamental frequency waveform. In the power spectrum, the second harmonic component is apparent. The power level of the second harmonic component is comparable with that of the fundamental component.

Pulse-Doppler Mode:

A typical response of masses of UCA bubbles to the Pulse-Doppler Mode is graphically illustrated as an effective RT curve in FIG. 27. Pulse-Doppler Mode is different than the B-Mode, in both its higher central frequency (about 2.4 MHz) and longer pulse length. In the Pulse-Doppler Mode, the lowest available acoustic driving power (MI) in the instrument employed in the multiple bubbles testing is 0.04. The change of modality applies acoustic pulses of different fundamental frequency and pulse length to the UCA bubbles. FIG. 28 graphically illustrates the corresponding power spectrum, enabling the harmonic responses of UCA bubbles to be observed when stimulated in the Pulse-Doppler Mode. The second harmonic power and even higher harmonic power sometimes could be very strong. The detailed profile varies and may reflect the specialty of the local UCA bubbles.

FIG. 28 includes three data sets, collected using a driving power of MI=0.04 in the Pulse-Doppler Mode. The fundamental frequency component profiles resemble one another in these examples, while their details differ between data sets, as discussed above with respect to FIG. 21 (B-Mode). The second harmonic component (at about 5 MHz) can be strongly visualized at MI=0.04; and even the third harmonic component (at about 6.5 MHz) can be very significant. At a very low driving pressure, the fundamental frequency of the response of the UCA bubbles does not shift, as was observed in the B-Mode.

As noted above, UCA bubbles start to break or dissolve even at particularly low driving powers. While the extremely strong harmonic components FIG. 28 could possibly arise due to breaking bubbles, because the effective radius (not shown) in the data sets of FIG. 28 does not change before and after the acoustic pulses, and because there is no sudden increase of effective radius during the entire sequence, it appears that none of the UCA bubbles were broken during the insonification of the data sets. Thus, it is believed that the stronger harmonic components are due to intact UCA bubbles. Some vulnerable UCA bubbles that could be destroyed near a power at MI=0.04 might be driven extremely non-linearly to generate strong a harmonic power, even though there is no bubble that is destroyed.

FIG. 29 is a composite graphically illustrating the power spectrum of multiple UCA bubbles being driven by different acoustic power (MI) in the Pulse-Doppler Mode. In order to visualize the impact of the variation in the power levels, FIG. 29 illustrates the power spectrums of multiple UCA bubbles at the following different MI: 0.04, 0.05, 0.06, 0.08, 0.09, and 0.10. The UCA bubbles are intact in these examples. The following conclusions can be made. First, it is obvious that the fundamental frequency and second harmonic frequency components can be very strong. Again, there is no frequency shift as was observed in B-Mode at a low driving power. Second, sub-harmonic components can be identified easily in some examples. Third, as in the B-Mode, the generation of harmonic components in the responses of masses of UCA bubbles does not depend on the driving power when the targeted bubbles are intact.

M-Mode:

FIG. 30A graphically illustrates a typical response from a mass of UCA bubbles to M-Mode stimulation (i.e., an effective RT curve of UCA bubbles in M-Mode at MI=0.04), while FIG. 30B graphically illustrates a corresponding power spectrum. The M-Mode features a central frequency of 2.4 MHz, with a shorter pulse length. In the M-Mode, only extremely high power (MI) is applied, to focus on the destruction of UCA bubbles. FIG. 31 is a composite image that graphically illustrates consecutive effective RT curves of a mass of UCA bubbles responding to M-Mode stimulation. The driving power employed to collect the data for FIG. 31 was MI=0.7. In FIG. 31, the first acoustic pulse (segment 1) destroys a significant amount of UCA bubbles, and brings down the effective RT from about 28 µm, before the acoustic pulse, to about 20 µm just after. It was enlightening to note that a single pulse can indeed destroy UCA bubbles. It is also observed that the UCA bubbles oscillate with the driving pulse while they are breaking. The second acoustic pulse (segment 2) causes more breakage, and brings down the effective RT from about 21 µm to about 18 µm. Even though the degree of destruction decreases, the third acoustic pulse (segment 3) and the fourth acoustic pulse (segment 4) continue breaking bubbles.

The data suggest that some UCA bubbles remain unbroken, even at very high driving powers. This phenomenon can be observed in the data for the fourth pulse (segment 4, FIG. 31), and in subsequent data (after segment 4) in the same data sequence, which is not shown. Compared with the data corresponding to FIGS. 25A and 25B, it is clear that higher acoustic pressure destroys UCA bubbles faster.

The multiple UCA bubble testing discussed above indicates that masses of UCA bubbles respond to acoustic waves, oscillate at even very low acoustic pressures, and generate a harmonic signal. The fundamental frequency of the response of masses of UCA bubbles can shift from that of a driving wave when the driving power is particularly low, which may reflect the characteristics of the local UCA bubbles. It was shown that the higher driving power does not provide an advantage with respect to generating harmonic responses of masses of UCA bubbles, when the driven UCA bubbles are intact. UCA bubbles can start to break at an extremely low driving power, as is known based on clinical practice. Higher acoustic driving levels will destroy UCA bubbles faster as expected, and such levels can destroy most UCA bubbles in a single pulse.

Summary and Conclusions:

To date, UCA bubbles have been studied mainly using acoustical methods. Significantly, in acoustical methods, the acoustic driving source will increase the background noise in the signal corresponding to the response of the UCA bubbles. An intrinsic property of acoustic transducers is the band-pass filtering of detected signals (the response of the UCA bubbles), which causes the spectral characteristics outside the pass band to be lost. To overcome these problems, the light scattering technique discussed above has been developed. The light scattering technique disclosed herein can be used to study the properties of individual UCA bubbles, or masses of UCA bubbles, when such bubbles are driven by acoustic pulses. Because UCA bubbles are so small, it is difficult to use light scattering techniques in UCA research, because the light scattering data collected are so noisy. Several techniques can be used to reduce noise. One technique involves focusing a laser beam to increase the incident light intensity, changing the beam width from about 3 mm to about 0.2 mm in diameter, which results in a 225-times increase in the incident light power density. Another technique is to use a collecting lens to cover a wide angle, and to collect more scattered light. The SNR can also be increased using signal processing techniques in data processing, including both averaging and filtering techniques.

The foundation of the light scattering technique is the Mie scattering theory. Empirical data indicates that the Mie theory is valid not only for homogeneous spheres, but also for coated spheres, such as UCA bubbles. Empirical data have confirmed that the thin-shelled UCA bubbles resemble homogeneous spheres in regard to scattering light. This result facilitates the processing and modeling of the light scattering data.

The empirical data discussed above with respect to single bubble studies show that the light scattering technique is a powerful tool for studying UCA bubbles, even though the SNR is challenging. Overcoming the SNR issue using the techniques noted above enables a response of UCA bubbles to different levels of acoustic driving signals to be observed successfully. One or more of the dynamic models discussed above can be used to fit the empirical data to the model, enabling UCA parameters to be calculated using the model. The empirical data demonstrated that UCA bubbles respond to acoustic driving pulses, and that UCA bubbles may undergo physical property changes. For example, Sonazoid™ bubbles increase in size during insonification, while other parameters, such as shell properties, remain unchanged. This phenomenon was confirmed in the corresponding power spectra of the response of the UCA bubble responses, where the fundamental frequency of the response of the bubbles decreases during the insonification. The increase in the UCA bubble's ambient radius suggests that the thin-shelled UCA bubbles can exchange gas through the shell membrane. They intake more gas from the surrounding medium, resulting in bigger bubbles.

The single bubble study also illustrates that UCA bubbles oscillate with driving pulses stably, even when the driving strength is weak. When the pulse length of the acoustic driving is longer, such as the examples with a single element transducer (HIFU transducer), the UCA bubble's oscillation tends to be stable when the acoustic driving pressure is stable. However, when the driving strength is strong, UCA bubbles will eventually be destroyed. By interpreting experimental data with the dynamic model, the destruction of UCA bubbles is well illustrated. The data indicate that the shells of UCA bubbles are distorted before the bubbles are destroyed. The ratio of the maximum radius to the ambient radius of UCA bubbles remains relatively constant when the UCA bubbles are intact. A sudden increase in this ratio occurs when UCA bubbles start to break up, and the ratio increases further afterwards. From the power spectra of the response of the UCA bubbles, it can be concluded that both harmonic and sub-harmonic components are generated when acoustic pulses drive UCA bubbles. Sometimes, the higher harmonic power is strong enough to be comparable with that of fundamental and second harmonic components.

Additional studies directed to using scattered light from masses of UCA bubbles employs an effective radius to account for interaction among the mass of bubbles. The empirical data indicate multiple UCA bubbles behave similarly to individual UCA bubbles, while due to the spatial distribution of the bubbles, interaction among the UCA bubbles and scattering of incident light and ultrasound, variations between individual UCA bubbles are also observed. Thus, the techniques disclosed herein can also be applied to study masses of UCA bubbles.

The results from the multiple bubble study indicate that the harmonic components of UCA bubbles' response can be generated at an extremely low driving pressure. This finding indicates that harmonic components can be generated whenever bubbles are forced to oscillate. Indeed, the oscillation will be slight when the driving pressure is weak. Therefore, the SNR becomes a critical factor at relatively lower driving pressure levels. In some cases, higher harmonic components, such as second, third, and even fourth harmonic components, can be very significant, compared to the fundamental components. The multiple bubble study also revealed that the response of a group of UCA bubbles can be different at a low driving pressure as compared with a higher driving pressure. In the B-Mode, the fundamental frequency of the response of the mass of UCA bubbles shifts to a lower frequency, when the driving power is lower than MI=0.05, which indicates that the self-resonant oscillation of UCA bubbles plays a role in this phenomenon. When the oscillation due to the acoustic wave is not strong, the self-resonant oscillation is comparable to the forced oscillation, so that the power spectrum of the combined oscillation of UCA bubbles is different than that of the acoustic driving pressure. However, when the forced oscillation is strong, it dominates, and the power spectrum of the response of the mass of UCA bubbles resembles that of the driving pressure.

In practice, UCA bubbles are vulnerable, and are easy to break, even at an extremely low pressure. Some of the UCA bubbles in a mass of bubbles start to break at MI=0.04. This phenomenon can be successfully observed using the light scattering technique disclosed above. A sudden increase of effective radius indicates the destruction of one or more UCA bubbles, and the release of their inner gas core. The corresponding power spectrum confirms this finding. When the driving power is strong, more UCA bubbles are expected to break during a given time interval. A particularly strong acoustic driving pressure can destroy many UCA bubbles with a single pulse. The surviving bubbles are further destroyed in a second pulse. Significantly, the UCA bubbles respond to the driving pulse even while they are being destroyed.

In conclusion, the light scattering technique disclosed herein can be used as a powerful tool to study and determine UCA shell parameters. The empirical data discussed above demonstrate the following:

The light scattering technique disclosed herein is an excellent tool to study UCA bubbles.
UCA bubble dynamics are correctly modeled with various dynamic models.
Individual UCA bubbles respond to acoustic driving pressure and undergo development during insonification.
Both the harmonic and sub-harmonic components of the response of an individual UCA bubble can be generated when it is forced to oscillate.
Imaging an individual UCA bubble with diagnostic ultrasound is feasible.
The harmonic component of the response of masses of UCA bubbles can be generated when bubbles in the mass are forced to oscillate.
Light scattering can be used to observe UCA bubbles breaking at an MI=0.04.
Very strong acoustic pressure can destroy most UCA bubbles in a mass of bubbles in a single acoustic pulse.

It should be recognized that existing particle sizing instruments can be modified to implement the concepts disclosed herein. Conventional particle sizing instruments use light scattering to determine the radius of one or more particles. Significantly, these instruments are designed to collect light scattering data from particles while the particles are static (i.e., while the particles are not experiencing changing pressure conditions). These instruments will be referred to herein and the claims that follow as static light scattering particle sizing instruments.

Such static light scattering particle sizing instruments can be modified by incorporating a pressure generator configured to induce pressure changes in a sampling volume in which the particles from which the scattered light is being collected are disposed. For example, an ultrasound imaging probe can be inserted into the sampling volume, such that when the ultrasound imaging probe is energized, the particles in the sampling volume will experience changing pressure conditions. Ultrasound instruments or ultrasound transducers can be also positioned externally of, but acoustically coupled to, the sampling volume. Preferably, a sensor configured to measure the pressure changes in the sampling volume (such as the hydrophone described above) will also be added to the existing static light scattering particle sizing instruments.

The processing required to generate the RT curves, to fit the curves to dynamic models, and to derive shell parameters can be implemented by an additional processor, or the processor for the static light scattering particle sizing instrument can be modified (i.e., reprogrammed) to implement the additional functions.

Yet another aspect of collecting scattered light from one or more microbubbles during changing pressure conditions, is that the resulting data can be used to differentiate different types of microbubbles based on their different compressibility (as microbubbles of different compressibility will exhibit different changes in their respective diameters), because as discussed above, light scattering can be used to detect changes in diameters. Bubbles having a larger radius will scatter more light than bubbles having a smaller radius, and bubbles that are less compressible will exhibit larger radii than bubbles which are more compressible, during increased pressure conditions, enabling light scattering data to be used to differentiate microbubbles based on their compressibility.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A system for measuring properties of microbubble shells using light scattering, comprising:
(a) a sampling volume configured to accommodate one or more microbubbles, wherein each such microbubble includes a microbubble shell comprising a physical membrane separating a volume of gas within the microbubble from a surrounding fluid, the sampling volume including a region of interest;

(b) an acoustic driving section configured to deliver an acoustic pressure into the sampling volume, such that the acoustic pressure intersects with the region of interest;

(c) a light providing section configured to illuminate the region of interest;

(d) a light collecting section configured to capture light scattered by one or more microbubbles in the region of interest; and (e) a processor coupled with the light collecting section, the processor being configured to determine at least one property of the one or more microbubbles in the region of interest, the processor being configured to implement the following functions:

(i) controlling the acoustic driving section such that a pressure change is caused in the region of interest, and such that scattered light is collected from the one or more microbubbles during changing pressure conditions;

(ii) correlating relative scattered light intensity changes collected by the light collecting section during the changing pressure conditions with a radius of the one or more microbubbles to generate a radius and time relationship for tracking changes in the radius of the one or more microbubbles in the region of interest over time; and (iii) fitting the radius and time relationship to a dynamic model for describing the motion of a microbubble, to determine a fitted relationship, where the dynamic model includes at least one parameter corresponding to the physical membrane.

2. The system of claim 1, wherein the processor is configured to determine one or more properties of the physical membrane using the fitted relationship.

3. The system of claim 1, further comprising a pressure sensor configured to determine a pressure in the region of interest, the pressure thus determined reducing a number of unknown variables in a dynamic model used by the processor in connection with data collected by the light collection section, to determine the at least one property of the one or more microbubbles in the region of interest.

4. The system of claim 1, further comprising an imaging section comprising a microscope, the imaging section being configured to determine an initial radius of the one or more microbubbles in the region of interest.

5. The system of claim 1, wherein the acoustic driving section comprises an ultrasound transducer.

6. The system of claim 1, wherein the sampling volume is filled with a viscous fluid, to facilitate the collection of scattered light from a single microbubble.

7. The system of claim 1, wherein the light providing section comprises a laser, light produced by the laser being focused to increase a light intensity incident on the region of interest, by reducing a beam width of the light produced by the laser.

8. The system of claim 1, wherein the light collecting section comprises a lens configured to collect light scattered by one or more microbubbles in the region of interest, and a photo multiplier tube configured to receive light from the lens.

9. The system of claim 8, wherein the lens is configured to collect scattered light having a scattering angle ranging from about 70 degrees to about 90 degrees from forward scattering.

10. The system of claim 1, further comprising an injection system configured to inject one or more microbubbles into the region of interest.

11. A system for measuring properties of microbubble shells using scattered light, comprising:

(a) a sampling volume configured to accommodate a microbubble having a shell comprising a physical membrane separating a volume of gas within the microbubble from an ambient fluid, the sampling volume including a region of interest;

(b) an injection system configured to introduce the microbubble into the region of interest;

(c) an acoustic driving section configured to deliver an acoustic pressure into the sampling volume, such that the acoustic pressure intersects with the region of interest;

(d) a light providing section configured to illuminate the region of interest;

(e) a light collecting section configured to capture light scattered by the microbubble in the region of interest; and (f) a processor coupled with the light collecting section, the processor being configured to determine at least one property of the physical membrane of the microbubble in the region of interest, based upon light scattered by the microbubble that is captured by the light collecting section, the processor being configured to implement the following steps:

(i) controlling the acoustic driving section such that a pressure increase is induced in the region of interest, and such that scattered light is collected by the light collecting section from the microbubble during changing pressure conditions;

(ii) correlating relative scattered light intensity changes collected during the changing pressure conditions with a radius of the microbubble;

(iii) generating a radius and time relationship for tracking changes to the radius of the microbubble in the region of interest over time;

(iv) fitting the radius and time relationship to a dynamic model for describing the motion of the microbubble, producing a fitted relationship, wherein the dynamic model includes at least one parameter corresponding to the physical membrane; and (v) determining one or more properties of the physical membrane of the microbubble using the fitted relationship.

12. A method for measuring properties of microbubble shells using scattered light, comprising the steps of:

(a) collecting light scattered from a microbubble having a shell comprising a physical membrane separating a volume of gas within the microbubble from an ambient fluid during changing pressure conditions experienced by the microbubble;

(b) correlating relative scattered light intensity changes collected during the changing pressure conditions with a radius of the microbubble;

(c) generating a radius and time relationship for tracking changes to the radius of the microbubble in the region of interest over time;

(d) fitting the radius and time relationship to a dynamic model for describing the motion of the microbubble, to produce a fitted relationship, wherein the dynamic model includes at least one parameter corresponding to the physical membrane; and (e) determining one or more properties of the physical membrane using the fitted relationship.

13. The method of claim 12, further comprising the step of reducing a number of unknowns in the dynamic model by empirically measuring at least one dynamic model parameter before fitting the radius and time relationship to a dynamic model.

14. The method of claim 13, wherein the step of empirically measuring at least one dynamic model parameter comprises the step of measuring pressure experienced by the microbubble.

15. The method of claim 13, wherein the step of empirically measuring at least one dynamic model parameter comprises the step of measuring an initial radius of the microbubble.

16. The method of claim 12, further comprising the step of reducing a number of unknowns in the dynamic model by employing an accepted value for at least one dynamic model parameter before fitting the radius and time relationship to a dynamic model.

17. The method of claim 12, further comprising the step of reducing an amount of noise in a signal corresponding to the scattered light that is collected, by increasing an intensity of light that is incident on the microbubble.

18. The method of claim 12, further comprising the step of reducing an amount of noise in a signal based on the scattered light that is collected, by using a lens to increase an amount of scattered light that is collected.

19. The method of claim 12, wherein before the step of collecting light, implementing the step of modifying a static light scattering particle sizing apparatus by adding a pressure generator configured to change a pressure in a sampling volume containing the microbubble, such that the modified static light scattering particle sizing apparatus is used to implement the step of collecting light.

20. The method of claim 19, wherein the step of modifying the static light scattering particle sizing apparatus by adding a pressure generator comprises the step of adding an ultrasound generating component to the static light scattering particle sizing apparatus.

21. The method of claim 12, wherein before the step of collecting light, implementing the step of modifying a static light scattering particle sizing apparatus by adding a pressure generator configured to change a pressure in a sampling volume containing the microbubble and programming the modified static light scattering particle sizing apparatus to implement steps (a) - (e).

22. The method of claim 12, wherein the step of collecting light scattered from the microbubble during changing pressure conditions experienced by the microbubble comprises the step of changing the pressure conditions using ultrasound waves exemplary of diagnostic ultrasound.

23. The method of claim 12, wherein the step of collecting light scattered from the microbubble during changing pressure conditions experienced by the microbubble comprises the step of changing the pressure conditions uni-directionally.

24. The method of claim 12, further comprising the step of using the collected light to differentiate the microbubble from other microbubbles based on compressibility.

25. A method for differentiating a plurality of shelled microbubbles using scattered light, comprising the steps of:
(a) collecting light scattered from the plurality of shelled microbubbles, each microbubble having a shell comprising a physical membrane separating a volume of gas within the microbubble from an ambient fluid during changing pressure conditions experienced by the microbubble; and
(b) for each shelled microbubble:
  (i) correlating relative scattered light intensity changes collected during the changing pressure conditions with a radius of the shelled microbubble;
  (ii) generating a radius and time relationship for tracking changes to the radius of the shelled microbubble in the region of interest over time; and
  (iii) correlating the radius and time relationship to a compressibility of the shelled microbubble, such that the compressibility can be used to differentiate the plurality of shelled microbubbles.

26. A system for differentiating a plurality of shelled microbubbles using scattered light, comprising:
(a) a sampling volume configured to accommodate one or more shelled microbubbles, wherein each such shelled microbubble includes a microbubble shell comprising a physical membrane separating a volume of gas within the microbubble from a surrounding fluid, the sampling volume including a region of interest;
(b) an acoustic driving section configured to deliver an acoustic pressure into the sampling volume, such that the acoustic pressure intersects with the region of interest;
(c) a light providing section configured to illuminate the region of interest;
(d) a light collecting section configured to capture light scattered by one or more microbubbles in the region of interest; and
(e) a processor coupled with the light collecting section, the processor being configured to differentiate the plurality of microbubbles based on optical scattering data, the processor being configured to implement the following function for each shelled microbubble:
  (i) correlating relative scattered light intensity changes collected during the changing pressure conditions with a radius of the shelled microbubble;
  (ii) generating a radius and time relationship for tracking changes to the radius of the shelled microbubble in the region of interest over time; and
  (iii) correlating the radius and time relationship to a compressibility of the shelled microbubble, such that the compressibility can be used to differentiate the plurality of shelled microbubbles.

* * * * *